(12) United States Patent
Bail et al.

(10) Patent No.: US 12,329,588 B2
(45) Date of Patent: Jun. 17, 2025

(54) SURGICAL VIRTUAL REALITY USER INTERFACE

(71) Applicant: Vicarious Surgical Inc., Waltham, MA (US)

(72) Inventors: Jeffrey Bail, Watertown, MA (US); Adam Sachs, Somerville, MA (US); Maxim Antinori, Arlington, MA (US)

(73) Assignee: Vicarious Surgical Inc., Waltham, MA (US)

( * ) Notice: Subject to any disclaimer, the term of this patent is extended or adjusted under 35 U.S.C. 154(b) by 414 days.

(21) Appl. No.: 17/774,372

(22) PCT Filed: Nov. 5, 2020

(86) PCT No.: PCT/US2020/059137
§ 371 (c)(1),
(2) Date: May 4, 2022

(87) PCT Pub. No.: WO2021/092194
PCT Pub. Date: May 14, 2021

(65) Prior Publication Data
US 2022/0387128 A1 Dec. 8, 2022

Related U.S. Application Data

(60) Provisional application No. 62/933,873, filed on Nov. 11, 2019, provisional application No. 62/930,922, filed on Nov. 5, 2019.

(51) Int. Cl.
*A61B 90/00* (2016.01)
*A61B 34/00* (2016.01)
(Continued)

(52) U.S. Cl.
CPC .............. *A61B 90/36* (2016.02); *A61B 34/20* (2016.02); *A61B 34/25* (2016.02); *A61B 34/37* (2016.02);
(Continued)

(58) Field of Classification Search
CPC ......... A61B 90/36; A61B 34/20; A61B 34/25; A61B 34/37; A61B 34/74;
(Continued)

(56) References Cited

U.S. PATENT DOCUMENTS 6,014,580 A * 1/2000 Blume ................... A61B 34/73
600/429
7,190,378 B2 3/2007 Sauer et al.
(Continued)

FOREIGN PATENT DOCUMENTS

| CN | 109099902 A | 12/2018 |
| JP | 2017-514608 A | 6/2017 |

(Continued)

OTHER PUBLICATIONS

European Office Action for Application No. 20884879.6, dated Sep. 13, 2023, 16 pages.
(Continued)

*Primary Examiner* — Sheree N Brown
(74) *Attorney, Agent, or Firm* — McCarter & English, LLP

(57) ABSTRACT

A surgical virtual reality user interface generating system can comprise a sensor and tracking unit for sensing and tracking a position of a portion of a user and generating position data based on movement of the user, a computing unit for receiving and processing the position data and generating control signals. The system can also include a surgical robot system for receiving the control signals and having a camera assembly for generating image data, and a
(Continued)

virtual reality computing unit for generating a virtual reality world. The virtual reality computing unit can include a virtual reality rendering unit for generating an output rendering signal for rendering the image data, and a virtual reality object generating unit for generating virtual reality informational objects and emplacing the informational objects in the virtual reality world. A display unit can display the virtual reality world and the informational objects to the user.

34 Claims, 15 Drawing Sheets

(51) Int. Cl.
  *A61B 34/20* (2016.01)
  *A61B 34/37* (2016.01)
  *G06F 3/01* (2006.01)
(52) U.S. Cl.
  CPC .............. *A61B 34/74* (2016.02); *G06F 3/011* (2013.01); *A61B 2034/2057* (2016.02); *A61B 2034/256* (2016.02); *A61B 2034/743* (2016.02); *A61B 2090/365* (2016.02); *A61B 2090/368* (2016.02)
(58) Field of Classification Search
  CPC ...... A61B 2034/2057; A61B 2034/256; A61B 2034/743; A61B 2090/365; A61B 2090/368; A61B 2017/00207; A61B 2017/00216; A61B 2034/105; A61B 2034/107; A61B 2034/303; A61B 2090/371; A61B 2090/372; A61B 2090/502; A61B 34/77; A61B 2034/742; A61B 2034/2048; A61B 90/361; G06F 3/011; G06F 3/012; G06F 3/013; G06F 3/0346; G06F 3/017; G02B 2027/0138; G02B 2027/014; G02B 27/01; H04N 13/239; H04N 13/279
  USPC ......................................................... 345/633
  See application file for complete search history.

(56) References Cited

U.S. PATENT DOCUMENTS

| | | | | |
|---|---|---|---|---|
| 8,332,072 | B1 * | 12/2012 | Schaible | A61B 34/74 606/1 |
| 8,521,331 | B2 * | 8/2013 | Itkowitz | A61B 34/30 606/1 |
| 8,730,156 | B2 * | 5/2014 | Weising | G06F 3/0304 348/47 |
| 8,970,625 | B2 * | 3/2015 | Chavez | H04N 13/111 345/419 |
| 9,123,155 | B2 * | 9/2015 | Cunningham | G16H 40/63 |
| 9,993,305 | B2 * | 6/2018 | Andersson | A61B 17/1757 |
| 10,008,017 | B2 * | 6/2018 | Itkowitz | G06T 11/40 |
| 10,146,335 | B2 * | 12/2018 | Balan | H04N 13/344 |
| 10,285,765 | B2 * | 5/2019 | Sachs | A61B 17/00234 |
| 10,398,513 | B2 * | 9/2019 | Razzaque | A61B 18/20 |
| 10,559,117 | B2 * | 2/2020 | Kaeser | G06T 19/003 |
| 10,852,838 | B2 * | 12/2020 | Bradski | G06F 3/014 |
| 11,412,951 | B2 * | 8/2022 | Piron | A61B 5/065 |
| 11,464,575 | B2 * | 10/2022 | Heaney | A61B 90/37 |
| 2002/0147455 | A1 * | 10/2002 | Carson | A61B 90/36 606/130 |
| 2011/0118748 | A1 | 5/2011 | Itkowitz | |
| 2011/0216060 | A1 | 9/2011 | Weising et al. | |
| 2013/0038707 | A1 * | 2/2013 | Cunningham | H04N 7/183 382/131 |
| 2014/0055489 | A1 * | 2/2014 | Itkowitz | G06T 11/40 345/633 |
| 2014/0171962 | A1 * | 6/2014 | Kang | A61B 90/10 606/130 |
| 2014/0275760 | A1 * | 9/2014 | Lee | A61B 1/00045 600/102 |
| 2014/0354689 | A1 * | 12/2014 | Lee | G06T 19/006 345/633 |
| 2015/0224639 | A1 * | 8/2015 | Dockter | B25J 3/04 700/264 |
| 2016/0214011 | A1 | 7/2016 | Weising et al. | |
| 2016/0292925 | A1 | 10/2016 | Montgomerie et al. | |
| 2016/0338776 | A1 * | 11/2016 | Jaramaz | A61B 34/10 |
| 2017/0076199 | A1 | 3/2017 | Zhang et al. | |
| 2017/0181802 | A1 | 6/2017 | Sachs et al. | |
| 2017/0228922 | A1 | 8/2017 | Kaeser et al. | |
| 2017/0296292 | A1 * | 10/2017 | Mahmood | G03H 5/00 |
| 2017/0367771 | A1 | 12/2017 | Tako et al. | |
| 2018/0256256 | A1 | 9/2018 | May et al. | |
| 2018/0333210 | A1 * | 11/2018 | Nijkamp | A61B 34/20 |
| 2019/0008595 | A1 | 1/2019 | Popovic et al. | |
| 2019/0038978 | A1 * | 2/2019 | Rider | A63F 13/92 |
| 2019/0076199 | A1 | 3/2019 | Kline et al. | |
| 2019/0094981 | A1 | 3/2019 | Bradski et al. | |
| 2019/0167350 | A1 * | 6/2019 | Ferro | A61B 5/4887 |
| 2019/0278797 | A1 * | 9/2019 | Joshi | G06F 16/5854 |
| 2019/0282309 | A1 * | 9/2019 | Schaible | A61B 34/37 |
| 2019/0295325 | A1 | 9/2019 | Montgomerie et al. | |
| 2019/0307362 | A1 | 10/2019 | Piron et al. | |
| 2019/0355278 | A1 * | 11/2019 | Sainsbury | A61B 34/30 |
| 2020/0023192 | A1 * | 1/2020 | Lee | A61B 5/1077 |
| 2020/0090401 | A1 * | 3/2020 | Terrano | G06V 40/172 |
| 2021/0090315 | A1 * | 3/2021 | Gladkov | G06F 9/45512 |

FOREIGN PATENT DOCUMENTS

| | | |
|---|---|---|
| JP | 2019-506922 A | 3/2019 |
| WO | 2015/171614 A1 | 11/2015 |

OTHER PUBLICATIONS

International Preliminary Report on Patentability for Application No. PCT/US2020/059137, dated May 19, 2022, 11 pages.
International Search Report and Written Opinion for Application No. PCT/US2020/059137, dated Feb. 12, 2021, 11 pages.
U.S. Appl. No. 29/858,406, filed Oct. 31, 2022, Pending.
Japanese Office Action for Application No. 2022-522796, dated Feb. 4, 2025, 10 pages.

* cited by examiner

SURGICAL VIRTUAL REALITY USER INTERFACE

RELATED APPLICATIONS

The present application is a 35 U.S.C. 371 national stage filing of International Application PCT/US2020/059137, filed Nov. 5, 2020, and entitled Surgical Virtual Reality User Interface, which claims priority to U.S. provisional patent application Ser. No. 62/933,873, filed on Nov. 11, 2019, and entitled Surgical Virtual Reality User Interface, and further claims priority to U.S. provisional patent application Ser. No. 62/930,922, filed on Nov. 5, 2019, and entitled Hand Controller For Surgical Robotic System, the contents of which are herein incorporated by reference.

BACKGROUND OF THE INVENTION

The present invention generally relates to minimally invasive surgery, surgical robotic devices, and associated user interfaces, and more specifically relates to user interfaces for use in virtual reality minimally invasive surgical systems.

During surgery it is necessary for a surgeon to have access to a myriad of information including data on the patient, the patient's vital signs, operation tasks and plans, and equipment status, amongst other information and data. Additionally, it is also helpful for a surgeon to have access to different views of the operation site, as well as views of the operating room. In conventional minimally invasive surgery, as well as with existing robotic surgical systems, a surgeon is easily able to access this information by looking at different screens located around the operating room, as well as having an assistant relay any required or necessary information.

In virtual reality assisted surgery, the surgeon has the perception of being condensed inside a patient's body at a surgical site through the use of sophisticated virtual reality hardware and software. As used herein, the term "virtual reality surgery" is intended to refer to a surgery that employs one or more robotic devices and associated systems and the surgeon is presented with a virtual representation of reality. The robotic systems can employ one or more cameras that provide video data of the surgical site as well as other required environmental locations and the video data can be combined with or overlaid on other visual elements and presented to the surgeon so as to provide a virtual representation of the various sites and surroundings, thus creating or forming a virtual world. According to known systems, a surgical robot can be placed inside the patient and can be configured to replicate selected motions of the surgeon, such as motions associated with the head, arms and hands. In conjunction with three-dimensional visualization provided by a virtual reality display device, such as for example a head mounted display (HMD), the surgeon can view the surgical site and interact with the surgical robot as if the robotic arms have taken the form of the surgeon's arms and hands. During virtual reality surgery, a successful outcome can be predicated on maintaining an immersive and natural looking virtual reality user interface, thus allowing the surgeon to concentrate on the surgical procedure. However, when immersed in the user interface, the surgeon may feel removed from the outside or external environment and thus unable to access necessary information and views while performing the operation.

SUMMARY OF THE INVENTION

In order to maintain the immersive and natural virtual reality user interface, and to be able to allow the surgeon to access any desired information, the system of the present invention can employ a user interface that allows the surgeon to interact with the surgical robot, as well as access desired information and data without disconnecting and removing themselves from the virtual environment.

The present invention is directed to a surgical virtual reality user interface generating system that employs a VR object generating unit for generating virtual objects for placement in a virtual reality landscape or world. The virtual objects provide information associated with selected aspects of the system for presentation to the system user while immersed in the virtual world. For example, the objects can provide image data, including images or video feed data from the robot camera assembly, patient specific data, such as MRI or x-ray data, and environment data, such as data associated with the patient and user environment. The objects can be manipulated by the user and are switchable between various states or modes. The objects can also be docked or reside in a docking station for easy access by the user. The virtual world also displays to the user a master list of objects that lists or sets forth all of the available objects. The present invention is directed to a surgical virtual reality user interface generating system comprising a sensor and tracking unit for sensing and tracking a position of a portion of a user in space and for generating at least position data based on movement of the user, and a computing unit for receiving the position data, the computing unit having a processor for processing the position data, and a control unit for generating control signals in response to the processed position data. The system also includes a surgical robot system coupled to the computing unit for receiving the control signals and having a camera assembly having a pair of axially spaced apart cameras for generating image data, and a virtual reality computing unit for generating a virtual reality world, where the virtual reality computing unit includes a virtual reality rendering unit for receiving at least the image data from the camera assembly and generating an output rendering signal for rendering the image data for display, and a virtual reality object generating unit for generating one or more virtual reality informational objects and for emplacing the informational objects in the virtual reality world. The system further includes a display unit for displaying the virtual reality world and the informational objects to the user.

The surgical robot system further includes one or more robot arms, and a motor unit coupled to the camera assembly and to the robot arms for selectively moving the camera assembly and the robot arms in response to the control signals, The sensor and tracking unit comprises a hand controller or a head mounted display.

The hand controller comprises an elongated main body having a movable lever switch coupled thereto.

The movable lever switch is rotatable about the main body, the main body has a channel formed therein, the lever switch is rotatably mounted in the channel, and a finger loop attached thereto.

The system comprises a rest nub formed on the main body, and a plurality of actuatable buttons formed on the main body. The plurality of actuatable buttons comprises first and second elbow buttons for allowing, when actuated, the user to manipulate an elbow joint region of the robotic arms, an actuatable rest button for allowing the user, upon actuation, to decouple movement of the robotic arms relative to movement of an arm of the user, and a lock button that allows the user to lock the lever switch relative to the main body.

The surgical robot system generates camera data indicative of the position and orientation of the cameras of the camera assembly, and the image rendering unit renders the image data with the camera data.

The display unit generates display data indicative of the position and orientation of a head of the user, and wherein the VR rendering unit renders the image data with the display data.

The virtual reality object generating unit is configured to receive informational data from a data source and then implanting the informational data in the informational objects.

The informational data comprises data from the surgical robot system.

The informational data further comprises data from one or more external data sources, and the informational data from the external data sources can comprise one of video data from an external camera or informational data from one or more external medical devices.

The informational object is configured to be displayed in the virtual reality world in a free mode where the informational object is disposed at a selected fixed location, a docking mode where the informational object is disposed in a docking station, or an attached mode where the informational object is disposed so as to follow the user in the virtual reality world.

The virtual reality object generating unit is configured to generate in the virtual reality world the docking station, wherein the docking station is configured to include a plurality of the informational objects.

The docking station has a plurality of virtual slots formed therein.

The virtual reality computing unit is configured to generate in the virtual reality world the docking station, wherein the docking station is configured to include a plurality of slots, each of which is configured to house one or more of the plurality of informational objects, and wherein when the informational object is removed from the slot by the user the informational object is automatically switched to the free mode.

The virtual reality object generating unit generates an object list having a list of the informational objects, wherein each of the plurality of informational objects in the object list includes a title of the object.

The informational object includes a title bar and a content region for displaying data, wherein the title bar includes a title of the informational object and a plurality of action buttons.

The plurality of action buttons comprises two or more of an auto visibility button which allow the user to determine if the object is visible or not in the virtual world, an object mode button that allows the user to switch object modes, a docking station button that allows the user to move the object into the docking station, and a close button that hides the object.

The virtual reality computing unit further comprises a photosphere generation unit for generating a photosphere from the image data.

The control unit is configured to generate an autoscan signal that is received by the camera assembly, and the camera assembly in response operates in an autoscan mode where the cameras in the camera assembly autonomously rotate through an entire range of motion to capture the image data.

The virtual reality computing unit further comprises a scene graph generating unit for generating a scene graph, wherein the scene graph includes a plurality of nodes arranged in a tree graph structure.

A method of generating one or more informational objects comprises sensing and tracking at least a position of a portion of a user in space and for generating position data based on movement of the user, providing a computing unit for receiving and processing the position data and generating control signals in response to the processed position data, providing a surgical robot system for receiving the control signals and having a camera assembly having a pair of axially spaced apart cameras for generating image data, generating a virtual reality world with a virtual reality computing unit, where the virtual reality computing unit includes a virtual reality rendering unit for receiving at least the image data from the camera assembly and generating an output rendering signal for rendering the image data for display, and a virtual reality object generating unit for generating one or more virtual reality informational objects and for emplacing the informational objects in the virtual reality world, and displaying the virtual reality world and the informational objects to the user. The surgical robot system further comprises one or more robot arms, and a motor unit coupled to the camera assembly and to the robot arms for selectively moving the camera assembly and the robot arms in response to the control signals.

The sensor and tracking unit comprises a hand controller or a head mounted display.

The hand controller comprises an elongated main body having a movable lever switch coupled thereto, the movable lever switch is rotatable about the main body, the main body has a channel formed therein and the lever switch is rotatably mounted in the channel.

The method comprises providing a plurality of actuatable buttons formed on the main body, and wherein the plurality of actuatable buttons comprises first and second elbow buttons for allowing when actuated the user to manipulate an elbow joint region of the robotic arms, an actuatable rest button for allowing the user, upon actuation, to decouple movement of the robotic arms relative to movement of an arm of the user, and a lock button that allows the user to lock the lever switch relative to the main body.

The virtual reality object generating unit is configured to receive informational data from a data source and then implanting the informational data in the informational objects.

The informational data comprises data from the surgical robot system.

The informational data further comprises data from one or more external data sources, and wherein the informational data from the external data sources can comprise one or video data from an external camera and informational data from one or more external medical devices.

The informational object is configured to be displayed in the virtual reality world in a free mode where the informational object is disposed at a selected fixed location, a docking mode where the informational object is disposed in a docking station, or an attached mode where the informational object is disposed so as to follow the user in the virtual reality world.

The virtual reality object generating unit is configured to generate in the virtual reality world the docking station, wherein the docking station is configured to include a plurality of the informational objects.

The docking station has a plurality of virtual slots formed therein.

The virtual reality computing unit is configured to generate in the virtual reality world the docking station, wherein the docking station is configured to include a plurality of slots, each of which is configured to house one of the plurality of informational objects, and wherein when the informational object is removed from the slot by the user the informational object is automatically switched to the free mode.

The virtual reality object generating unit generates an object list having a list of the informational objects, wherein each of the plurality of informational objects in the object list includes a title of the object.

The informational object includes a title bar and a content region for displaying data, wherein the title bar includes a title of the informational object and a plurality of action buttons.

The plurality of action buttons comprises two or more of an auto visibility button which allows the user to determine if the object is visible or not in the virtual world, an object mode button that allows the user to switch object modes, a docking station button that allows the user to move the object into the docking station, and a close button that hides the object.

The virtual reality computing unit comprises a photosphere generation unit for generating a photosphere from the image data.

The control unit is configured to generate an autoscan signal that is received by the camera assembly, and the camera assembly in response operates in an autoscan mode where the cameras in the camera assembly autonomously rotate through an entire range of motion to capture the image data.

BRIEF DESCRIPTION OF THE DRAWINGS

These and other features and advantages of the present invention will be more fully understood by reference to the following detailed description in conjunction with the attached drawings in which like reference numerals refer to like elements throughout the different views. The drawings illustrate principals of the invention and, although not to scale, show relative dimensions.

DETAILED DESCRIPTION

Figure 1:
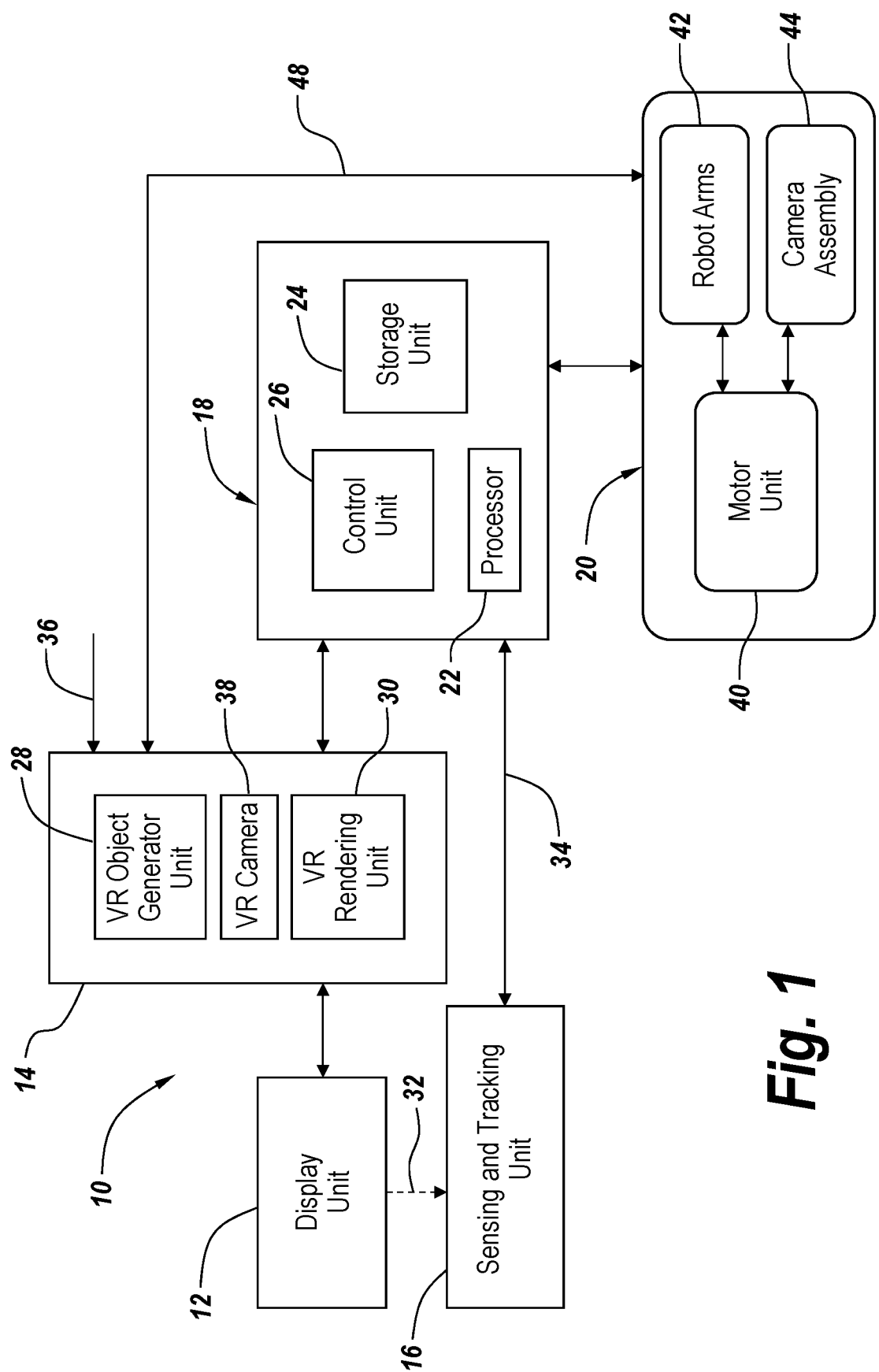
FIG. 1 is a schematic block diagram description of a surgical virtual reality user interface generating system according to the teachings of the present invention.

In the following description, numerous specific details are set forth regarding the systems and methods of the present invention and the environment in which the system and method may operate, in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that any examples provided below are merely illustrative and are not to be construed in a limiting manner, and that it is contemplated by the present inventors that other systems, apparatuses, and/or methods can be employed to implement the teachings of the present invention and that are deemed to be within the scope of the present invention.

While the systems and methods of the present invention can be designed for use with one or more surgical robotic systems employed as part of a virtual reality surgery, the system of the present invention may be employed in connection with any type of surgical system, including for example robotic surgical systems, straight-stick type surgical systems, and laparoscopic systems. Additionally, the system of the present invention may be used in other non-surgical systems, where a user requires access to a myriad of information, while controlling a device or apparatus.

The systems and methods disclosed herein can be incorporated and utilized with the robotic surgical device and system disclosed for example in U.S. Pat. No. 10,285,765 and PCT patent application Serial No. PCT/US20/39203, and/or with the camera system disclosed in United States Publication No. 2019/0076199, where the teachings of all of the foregoing publications are herein incorporated by reference. In some embodiments the surgical virtual reality user interface generating system can also be implemented and utilized by other existing and future surgical robotic systems or devices employing known visualization techniques, including for example virtual reality and/or augmented reality visualization techniques. The present invention can employ one or more surgical virtual reality user interface (SVRUI) generating systems that are designed to allow a user to emplace informational objects or widgets into a virtual reality (VR) environment that can be used to embody and to control one or more surgical robotic devices. As used herein, the term "informational object" or "widget" is intended to include any type of data, such as image data, informational data and the like, that is related to or associated with one or more real world objects. The objects or widgets can be manipulated by a user and can be displayed in one or more states. The objects can be virtual reality (VR) objects. The objects can also be multi-dimensional, and can for example display information in three-dimensional space. Further, the objects can include information that does not form part of the image data generated by the camera assembly. Based on three-dimensional models (3D) models, the data can include for example virtual representations of equipment, graphical data, patient data, 3D scans, or anatomy models. The user interface elements, floating virtual menus or screens can be passive or active elements, where the user can interact with them, or the objects can display information from another data sources. As further described herein, in some embodiments, the placement of the informational objects can be determined by the user via one or more selected controllers, such as handheld controllers, head mounted controllers, and eye tracking controllers, or by way of some other type of user input device, and the informational objects can be automatically arranged by the system in a selected manner or in or at any selected location in a virtual environment, such as for example in a docking station. The docking station can have a fixed or movable position relative to real world coordinates, either above a selected work or surgical site and/or attached directly to the user's head, in order to maintain a constant position and orientation with respect to a display device or unit, such as for example a display, a head mounted display (HMD) or a screen such as a 3-D screen, or the like.

In some embodiments the system of the present invention is part of a larger surgical system and is utilized to allow a user, such as a surgeon, to interact with the VR world and surgical robotic devices while concomitantly performing a virtual reality surgery using a surgical robotic device.

FIG. 1 is a schematic block diagram description of a surgical virtual reality user interface generating system 10 according to the teachings of the present invention. The system 10 includes a display device unit 12, a virtual reality (VR) computing unit 14, a sensing and tracking unit 16, a computing unit 18, and a surgical robotic system 20. The display unit 12 can be any selected typed of display for displaying information, images or video generated by the VR computing unit 14, the computing unit 18, and/or the surgical robot system 20. The display unit 12 can include for example a head-mounted display (HMD), a screen or display, a three-dimensional (3D) screen, and the like. The sensing and tracking unit 16 can include one or more sensors or detectors that are coupled to a user of the system, such as for example a nurse or a surgeon. The sensors can be coupled to the arms of the user, and if a head-mounted display is not used, then additional sensors can also be coupled to a head and/or neck region of the user. If the user employs a head-mounted display, then the eyes, head and/or neck sensors and tracking technology can be built-in or employed with that device. The sensors coupled to the arms of the surgeon can be preferably coupled to selected regions of the arm, such as for example the shoulder region, the elbow region, the wrist or hand region, and if desired the fingers. The sensors generate position data indicative of the position of the selected portion of the user. The sensing and tracking unit 16 utilized to control the camera assembly 44 may be separate and distinct from the sensing and tracking unit used to control the robotic arms. The position data 34 generated by the sensors can be conveyed to the computing unit 18 for processing by a processor 22. The computing unit 20 can determine or calculate from the position data the position and/or orientation of each portion of the surgeon's arm and convey this data to the surgical robot system 20. According to an alternate embodiment, the sensing and tracking unit 16 can employ sensors coupled to the torso of the surgeon or any other body part. Further, the sensing and tracking unit 16 can employ in addition to the sensors an Inertial Momentum Unit (IMU) having for example an accelerometer, gyroscope, magnetometer, and a motion processor. The addition of a magnetometer is standard practice in the field as magnetic heading allows for reduction in sensor drift about the vertical axis. Alternate embodiments also include sensors placed in surgical material such as gloves, surgical scrubs, or a surgical gown. The sensors may be reusable or disposable. Further, sensors can be disposed external of the user, such as at fixed locations in a room, such as an operating room.

In the embodiment where the display is a HMD, the display unit 12 can be for example a virtual reality head-mounted display, such as for example the Oculus Rift, the Varjo VR-1 or the HTC Vive Pro Eye. The HMD can provide the user with a head-mounted display, lenses to allow a focused view of the display, and a sensor and/or tracking system to provide position and orientation tracking of the display. The position and orientation sensor system can include for example accelerometers, gyroscopes, magnetometers, motion processors, infrared tracking, eye tracking, computer vision, emission and sensing of alternating magnetic fields, and any other method of tracking at least one of position and orientation, or any combination thereof. As is known, the HMD can provide image data from the camera assembly 44 to the right and left eyes of the surgeon. In order to maintain a virtual reality experience for the surgeon, the sensor system can track the position and orientation of the surgeon's head, and then relays the data to the computing unit 18. The computing unit 18 can further adjust the pan and tilt of the camera assembly 44 of the robot so as to follow the movement of the user's head.

The sensor or position data 32 generated by the sensors if associated with the display unit 12 can be conveyed to the computing unit 18. For purposes of simplicity, the sensor data 32 is shown being conveyed to the sensing and tracking unit 16, although one of ordinary skill in the art will readily recognize that the tracking and position data 32 can be conveyed directly to the computing unit 18. Alternatively, the tracking and position data 32 can be conveyed to the VR computing unit 14 and then conveyed to the computing unit 18 for further processing. Likewise, the tracking and position data 34 generated by the other sensors in the system, such as from the sensing and tracking unit 16 that can be associated with the user's arms and hands, can be conveyed to the computing unit 18. The tracking and position data 32, 34 can be processed by the processor 22 and can be stored for example in the storage unit 24. The tracking and position data 32, 34 can also be used by the control unit 26, which in response can generate control signals for controlling one or more portions of the surgical robot system 20. The surgical robot system 20 can comprise a surgical system that includes a user workstation, a robot support system (RSS), a motor unit 40, and an implantable surgical robot that includes one or more robot arms 42 and one or more camera assemblies 44. The implantable robot arms and camera assembly can form part of a single support axis robot system, such as that disclosed and described in U.S. Pat. No. 10,285,765, or can form part of a split arm architecture robot system, such as that disclosed and described in PCT patent application no. PCT/US20/39203.

The control signals generated by the control unit 26 can be received by the motor unit 40 of the surgical robot system 20. The motor unit 40 can include a series of servomotors that are configured for driving separately the robot arms 42 and the cameras assembly 44. The robot arms 42 can be controlled to follow the scaled-down movement or motion of the surgeon's arms as sensed by the associated sensors. The robot arms 42 can have portions or regions that can be associated with movements associated with the shoulder, elbow, wrist and fingers of the user. For example, the robotic elbow can follow the position and orientation of the human elbow, and the robotic wrist can follow the position and orientation of the human wrist. The robot arms 42 can also have associated therewith end regions that can terminate in end-effectors that follow the movement of one or more of fingers of the user, such as for example the index finger as the user pinches together the index finger and thumb. While the arms of the robot follow movement of the arms of the user, the robot shoulders are fixed in position. In one embodiment, the position and orientation of the torso of the user is subtracted from the position and orientation of the users arms. This subtraction allows the user to move his or her torso without the robot arms moving.

Figure 2:
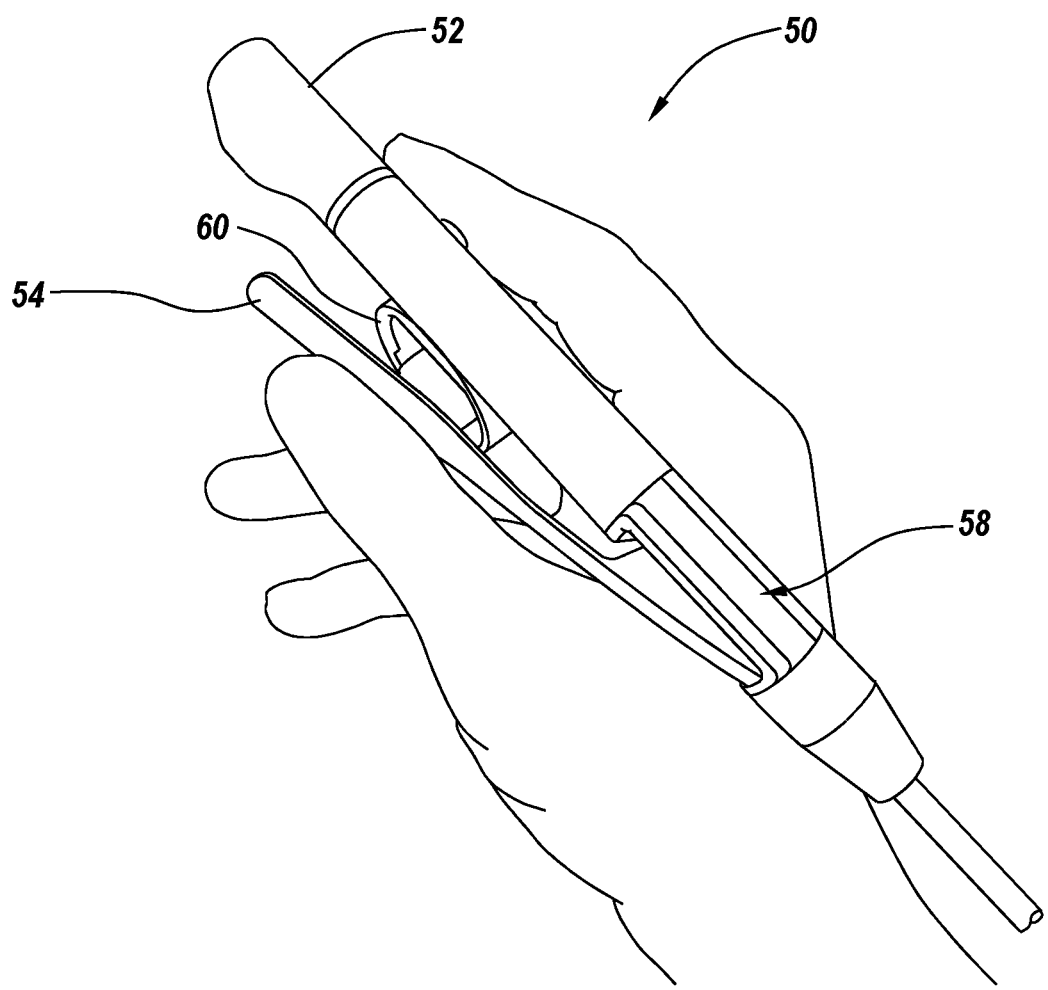
FIG. 2 is a depiction of a hand controller in use by a surgeon for controlling movement of robotic arms according to the teachings of the present invention.
Figure 3A:
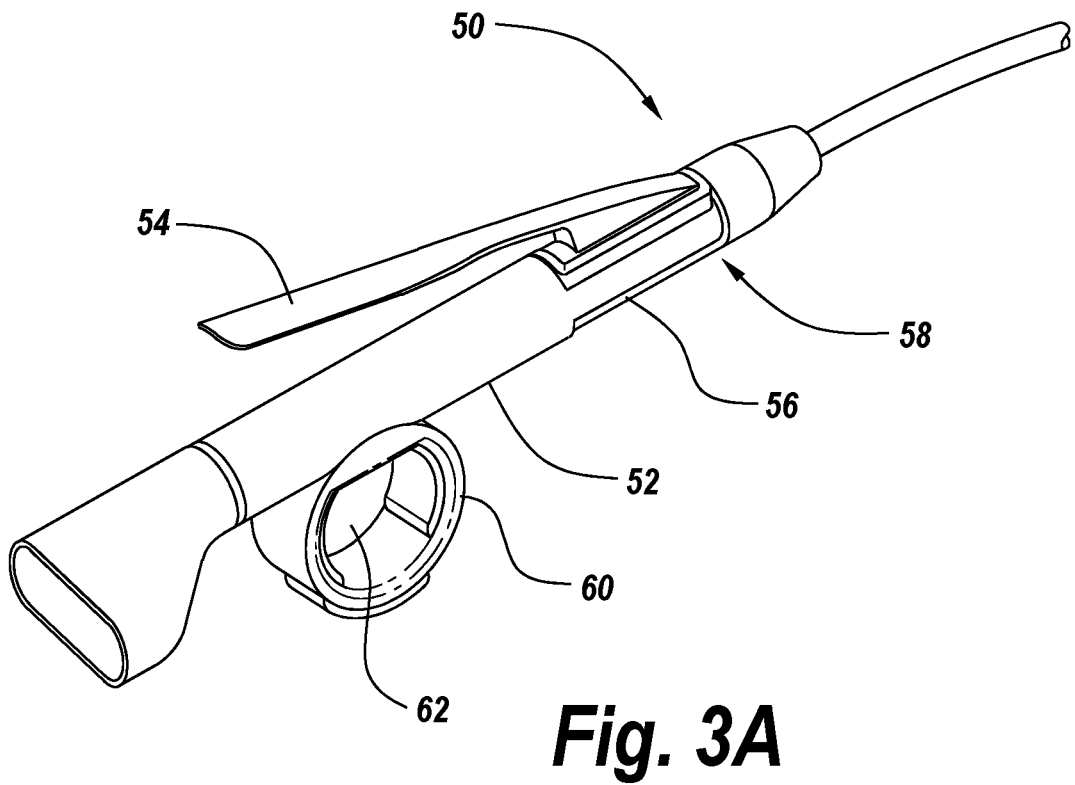
FIGS. 3A and 3B are perspective views of a hand controller according to the teachings of the present invention.
Figure 3B:
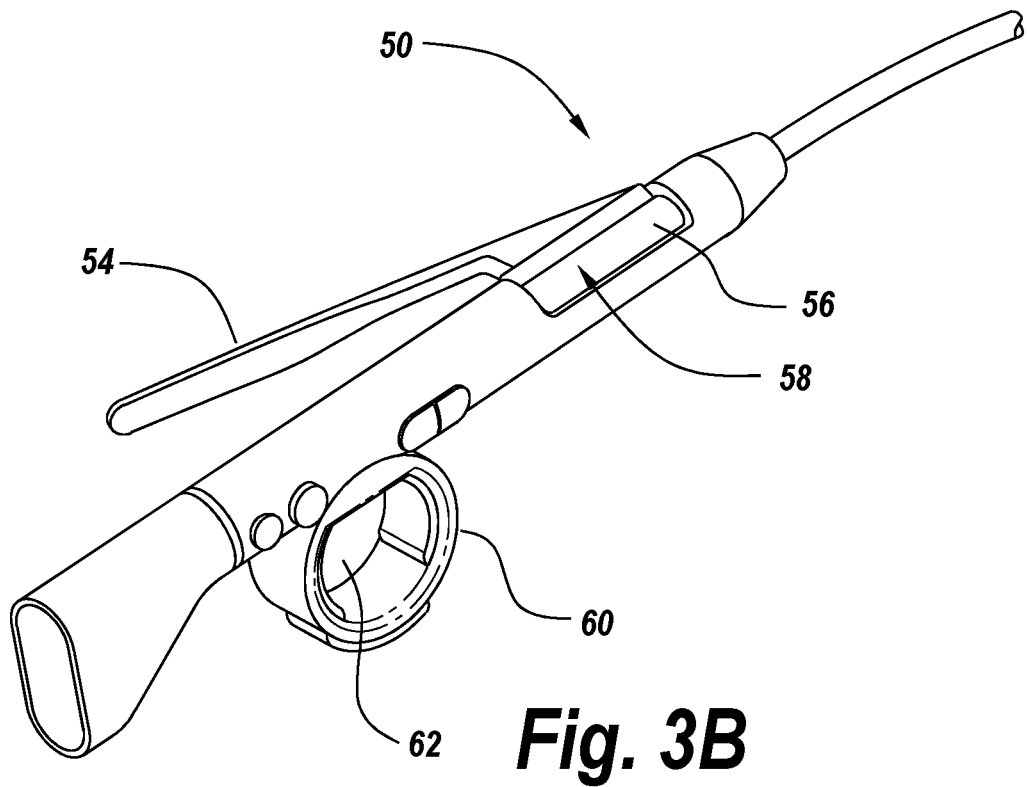
Figure 4:
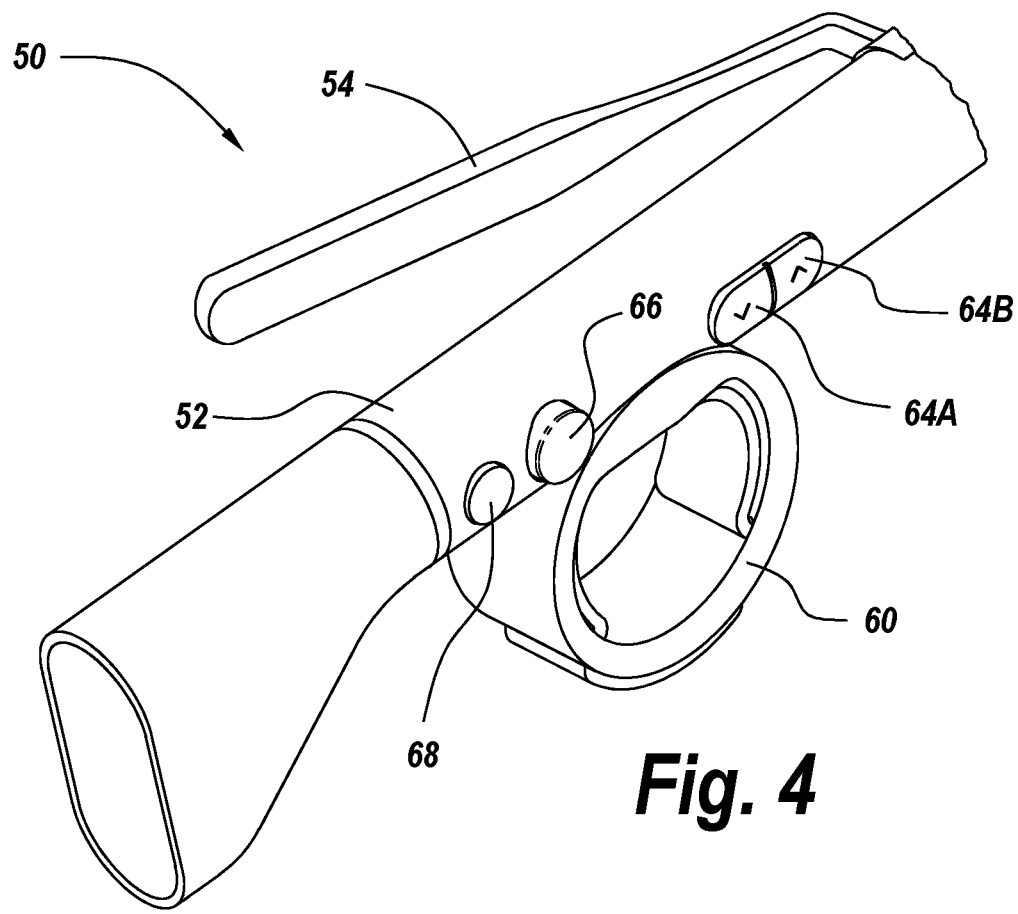
FIG. 4 is a partial perspective view of the hand controller of the present invention.

The user can also employ as part of the sensing and tracking unit 16 a hand controller that has one or more sensors or detectors associated therewith. An example of one type of hand controller suitable for use with the surgical robot system 20 is shown in FIGS. 2-4. Those of ordinary skill in the art will readily recognize that other known types of hand controllers can also be used. The illustrated hand controller 50 has a relatively slim profile and an elongated main body 52 that is sized and configured to fit comfortably within the hand of the user, such as a surgeon. As shown for example in FIG. 2, the hand controller 50 is typically held between the thumb and forefinger of the surgeon. The hand controller is adapted to generate signals that are processed by the computing unit 18. The controller 26 in response to the processed signals generates and sends control signals to the motor unit 40 that in turn controls the robot arms 42, such as for example the end effector regions of the robotic arms 42. The surgeon can thus control a grasping motion of the end effectors using any selected actuation mechanism, such as a switch, lever or the like, using any selected finger of the surgeon. As such, the hand controller 50 can serve to manipulate the end effectors of the robotic system, such as the ability to grasp (e.g., close) and release (e.g., open) the end effectors, move the end effectors outwardly and inwardly in an axial direction, as well as rotate the end effectors, all by using the hand controller 50 of the present invention.

The hand controller 50 also includes a movable lever switch 54 that is movable between a release position (FIG. 3A) where the lever switch 54 is not engaged and the end effectors of the robotic arms are open and an engaged position (FIG. 2) where the lever switch 54 is movable toward the main body 52 of the hand controller 50 which in turn actuates the end effectors to close or grasp an object. Specifically, when the user or surgeon squeezes the lever switch 54 against the main body 52 of the hand controller, the robotic arms can close the end effectors or take other robotic action.

The lever switch 54 can be coupled to a slip ring (not shown) or other sliding mechanism that allows the lever switch 54 to rotate about the main axis of the main body 52. The lever switch 54 is coupled to a rotatable connector 56 that allows the lever switch to move within a channel 58 formed in the main body. The edges of the channel 58 form the extent of the rotational movement of the lever switch 54. The channel 58 allows the surgeon to grasp and then rotate the end effector beyond the limits of movement of the human wrist by spinning or rotating the lever switch 54 around the body 52 of the controller and within the channel 58 while holding the controller in a stationary position.

The main body 52 of the hand controller 50 can also include a finger loop 60 for allowing the surgeon to insert a finger therein (FIG. 2) so as to provide a selected degree or amount of stability to the hand controller 50. The finger loop 60 can include if desired an adjustment mechanism associated therewith for allowing adjustment of the opening of the finger loop. This allows the surgeon to customize the size of the opening 62 in the finger loop 60 to better fit the inserted finger.

The hand controller 50 can also have a series of actuators or buttons associated therewith to allow the surgeon to manipulate or control movement of the robotic arms 42. For example, the main body 52 of the hand controller 50 can include one or more elbow buttons 64A, 64B that allow the surgeon to manipulate an elbow joint area or region of the robotic arm. The elbow buttons can thus allow the surgeon to bend the elbow region of the robotic arm in selected opposed directions by selectively actuating the buttons. Further, the illustrated hand controller 50 can also include an optional rest position nub or detent 66 that is sized and positioned to allow the surgeon to rest one or more fingers during use, so as to avoid accidental contact with one of the other actuatable buttons. According to an alternate embodiment, the nub 66 can be configured as an actuatable button that allows the surgeon, upon actuation, to decouple movement of the robotic arm relative to movement of the surgeon's arm. As such, the surgeon can actuate the button by pressing, thus disconnecting movement of the hand controller with the robotic arms. The hand controller can also include an optional lock button 68 that allows the surgeon to lock the lever switch 54, thus preventing accidental movement of the end effectors of the robot arms.

Further, the computing unit 18 can translate movement of the surgeon's arms into motion of the robot arms 42 with direct scaling. However, other embodiments may include adjustable scaling of the motion. That is, the scaling can be adjusted up or down. For example, the motion can be scaled down such that a movement of the surgeons elbow by ten degrees results in a similar movement of the device's elbow by five degrees. This scaling allows for increased dexterity in exchange for decreased natural feel of the device.

The robot camera assembly 44 is configured to provide the surgeon with image data 48, such as for example a live video feed of an operation or surgical site, as well as enable a surgeon to actuate and control the cameras constituting the camera assembly 44. The camera assembly 44 preferably includes a pair of cameras the optical axes of which are axially spaced apart by a selected distance, known as the inter-camera distance, so as to provide a stereoscopic view of the surgical site. The surgeon can control the movement of the cameras either through movement of a head mounted display or via sensors coupled to the head of the surgeon, or by using a hand controller or sensors tracking the user's head or arm motions, thus enabling the surgeon to obtain a desired view of an operation site in an intuitive and natural manner.

The cameras are movable in multiple directions, including for example in the yaw and pitch directions, as is known. In some embodiments the cameras are also moveable in a roll direction as well. The components of the stereoscopic cameras can be configured to provide a user experience that feels natural and comfortable. In some embodiments, the inter-axial distance between the cameras can be modified to adjust the depth of the operation site perceived by the user.

The camera assembly 44 is actuated by the movement of the surgeon's head. For example, during an operation, if the surgeon wishes to view an object located above the current field of view, the surgeon looks in the upward direction, which results in the stereoscopic cameras being rotated upward about a pitch axis from the user's perspective. The image or video data 48 generated by the camera assembly 44 can be displayed on the display unit 12. If the display unit 12 is a head-mounted display, the display can include built-in tracking and sensor systems that obtain raw orientation data for the yaw, pitch and roll directions of the HMD as well as positional data in Cartesian space (x, y, z) of the HMD. However, alternative tracking systems may be used to provide supplementary position and orientation tracking data of the display in lieu of or in addition to the built-in tracking system of the HMD. An example of a camera assembly suitable for use with the present invention includes the camera assemblies disclosed in U.S. Pat. No. 10,285,765 and U.S. Publication No, 2019/0076199, to the assignee hereof, the contents of which are incorporated herein by reference.

The image data generated by the camera assembly 44 can be conveyed to the virtual reality (VR) computing unit 14 and can be processed by the VR or image rendering unit 30. The image data 48 can include still photograph or image data as well as video data. The VR rendering unit 30 can include suitable hardware and software for processing the image data and then rendering the image data for display by the display unit 12, as is known in the art. Further, the VR rendering unit 30 can combine the image data received from the camera assembly 44 with information associated with the position and orientation of the cameras in the camera assembly and information associated with the position and orientation of the head of the surgeon. With this information, the VR rendering unit 30 can generate an output video or image rendering signal and transmit this signal to the display unit 12. That is, the VR rendering unit 30 renders the position and orientation readings of the hand controllers and the head position of the surgeon for display in the display unit, such as for example in a HMD worn by the surgeon.

The virtual reality (VR) object generator unit 28 of the VR computing unit 14 can be employed to generate the informational objects 82 for emplacement in the virtual reality world 100 that is displayed to the surgeon via the display unit 12. The informational objects 82 can be used to input informational data into the VR world for allowing the surgeon to readily access desired information while performing a surgery. The informational objects and associated informational data contained therein are sent to the VR computing unit 14 and then rendered into the display unit 12. In some embodiments of the present invention, the informational objects 82 can be entirely contained within the VR computing unit 14. In other embodiments of the present invention, the informational objects rely on information from other data sources in the system 10, such as for example from the surgical robot system 20 or data 36 from third party or external sources, in order to render or animate the display of the robot arms or other surgical devices. In still further embodiments, the data source is an external data source 36 that communicates with the VR computing unit 14 and can introduce thereto for example a video stream from an external camera disposed in the external environment, such as from a camera in the operating room or at a nurse's station. In another embodiment, the data source 36 can include data from medical devices or systems, such as from an MRI machine, one or more patient monitors (e.g., blood pressure level, heart rate, etc.), and the like. The data from the various data sources can be packaged into the informational object and can be inserted or rendered into the virtual reality world of the surgeon.

The surgical virtual reality user interface generating system 10 of the present invention can be configured to allow a user to interact with the VR world 100 generated by the VR computing unit 14 while performing a virtual reality surgery. According to one practice, the VR world 100 can be projected onto a screen of a head-mounted display worn by the user or can be transmitted and projected onto an interactive display or screen, such as for example a monitor in the operating room or a screen at a user workstation. In the VR world 100, the informational objects 82 are displayed on the HMD or on a 3D screen. The informational objects 82 are preferably virtual reality objects that can be manipulated by the user. According to one practice, the informational objects can display three-dimensional medical information, such as MRI information or CT imagery data, image data such as live video feed data or still images, and/or virtual objects. The virtual objects can be a computer generated three-dimensional representation of informational data, an object, or the like, that is placed inside a computer generated virtual reality world 100, and where the user can interact therewith and also interact with other objects in the VR world 100. If desired the virtual object can be viewed by the user via the display unit and can include virtual screens, virtual menus, virtual clocks, reference models of anatomy, overlays of 3D trajectories to follow, user placeable markers, measurement devices, and the like, or any tool or object that one can be uses in the real world can have a virtual analog that can provide utility in the virtual world while operating on the patient. In essence, the system 10 of the present invention can provide for an augmented telepresence experience in a virtual surgical environment, where the telepresence can include live camera feeds and the augmentation being any virtual overlays or interactions that can be provided along with the camera feed.

The informational objects can be displayed in different states depending on the user's desired configuration. According to one embodiment of the present invention, the informational objects can be displayed or configured to be in a free mode or state, a docking mode or state, and an attached mode or state. In the free state mode or state, the informational objects remain fixed at a specific location in the VR space. The objects can be disposed at a specific location in the VR world 100 by using the hand controller 50 or by movement of the hand or arm of the surgeon. The free state mode allows the surgeon to position specific objects at specific locations, and at a specific distance relative to the robot arms. Thus, from the user's perspective the informational or virtual object stay in place within the surgical field even as the camera FOV is moved about the field. The relative permanence of the objects makes the objects feel like part of the surgical field. For example, if the surgeon wishes to refer to a preoperative CT scan during a certain portion of an operation, the surgeon can temporarily place a CT specific informational object near the particular part of the surgical field that the CT scan is highlighting or referencing. The states or modes of the informational objects can be changed by selecting one or more soft buttons.

Figure 5:
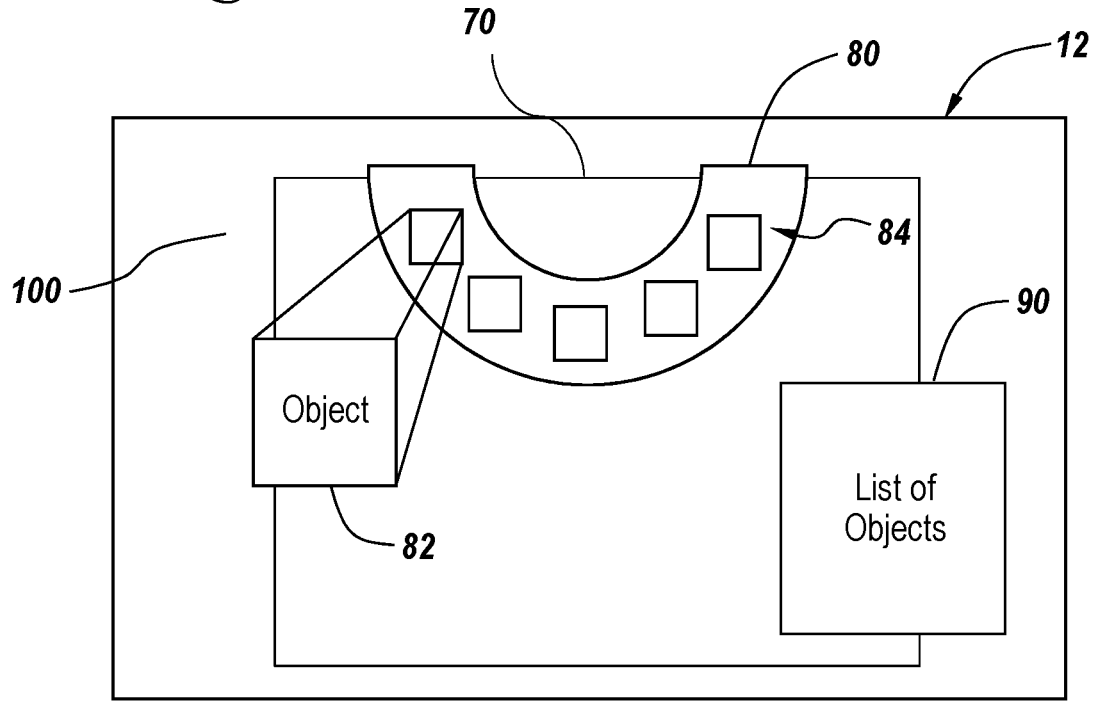
FIG. 5 is a schematic representation of a virtual reality world as viewed by a user via a display unit and showing informational objects and associated docking station according to the teachings of the present invention.

According to the teachings of the present invention, the informational objects can also be disposed or placed in a docking mode or state. FIG. 5 shows the display unit 12 that displays to the user a rendered view of the VR world 100 generated by the VR computing unit 14. The VR world 100 displays the video data and associated field of view (FOV) 70 of the camera assembly 44. The FOV 70 fills the entirety of the screen of the display unit 12 in some embodiments and in others the FOV only fills a portion of the screen of the display unit 12. In the docking mode, the informational objects or widgets 82 can be automatically arranged or docked in a docking station or container 80. The docking station 80 can have any selected shape or size and is preferably manipulatable by the user. Alternatively, the location of the docking station 80 can be predefined. According to one practice, the docking station 80 can have an arch-like or halo shape that allows the user to select one or more informational objects from a list of informational objects 90 to be placed in the docking station 80. Alternatively, the system 10 via the VR object generator unit 28 or the VR computing unit 14 can populate the docking station 80 with one or more preselected informational objects 82. The user can place the informational objects 82 that they desire to remain visible in a selected location in the VR world 100 that does not interfere and/or obstruct a view of the operation site without requiring the user to manually place each individual informational object 82 in the VR world 100. The docking station 80 can be configured to have a plurality of predefined locations or slots 84 for positioning the selected informational objects 82. The informational objects 82 can be dragged and rearranged by the user from slot to slot within the docking station 80 using the hand controller or any other selection method or technique. In one embodiment, the user can view a representation of the hand controller in the VR world 100, moves the hand controller representation over an informational object 82, presses and holds a button on the hand controller, and then moves the hand controller in order to drag the informational object. Once in the desired location, the user can release the button and the informational object is dropped in place in the VR world 100. The same action can be achieved by other similar interface elements known in the art, including but not limited to gesture tracking, eye and blink tracking, keyboard, mouse, voice activation, and the like.

When the user drags an informational object 82 within the display 12, a preview of the slot area that the informational object 82 can occupy is shown. In one embodiment, the preview of the slot 84 is shown in front of the docking station 80, and the preview can have any selected shape or size, such as a sphere. When the informational object 82 is dragged out of the slot 84 of the docking station 80, FIG. 5, the informational object 82 is automatically switched to free mode. If the informational object is in the free mode and the user desires to drag the informational object 82 back into a selected slot 84 of the docking station 80, the docking station 80 can optionally be highlighted and a preview of one of the slots 84 can be shown, and when the informational object 82 is dropped within a selected slot 84, the informational object switches from the free mode to the docking mode.

The docking station 80 can have a two-dimensional geometry or a three-dimensional geometry, and preferably can be configured to have the shape of a dissected torus. In one embodiment, the geometry of the docking station 80 is generated by suitable hardware and software in the VR object generator unit 28. The VR object generator unit 28 can include suitable hardware and software for generating the docking station and the informational objects or widgets and can include hardware to receive the external data 36. With regard to the docking station 80, the VR object generator unit 28 can be programmed to generate a docking station having a pre-defined shape and size, and the size of the docking station can be scaled by the user during use. Once the geometry of the docking station 80 is determined, the VR object generator unit 28 can generate the slots 84 by dividing the space of the docking station 80 into a predetermined manner to generate a selected number of slots 84 having a selected spacing therebetween. The docking station 80 can remain fixed in place above the working area in the display, while in other embodiments the docking station is draggable by the user to allow the user to reposition the docking station, as well as the widgets contained therein. The docking station 80 can be attached and/or docked to virtual objects in the VR world 100, such as for example a virtual workstation model.

The informational objects 82 can also be disposed in the attached mode or state. In the attached mode, the informational objects maintain a specific position and orientation relative to the display unit 12 (e.g., appears to move with the user), with the position and orientation of the informational objects 82 being specified by the user. In this mode, the informational objects 82 are always visible to the user no matter how the user adjusts their camera or view. In embodiments with an HMD, the appearance and sensation to the user is like having something stuck to the user's head such that when the user moves their head the informational object moves in a matching way such that it always stays in the same position and portion of the user's field of view. The attached mode also allows the user to place an informational object in their field of view so that it is constantly viewable without having to select the widget from the docking station 80 or locate the informational object 82 by moving their head as would be required when the informational object is in the free mode. In embodiments with a stationary screen, attached mode locks informational objects to a particular position and orientation relative to the screen. This is analogous to a heads-up-display.

In the system 10 of the present invention, the informational objects 82 can be preconfigured in any of the above modes, and one or more informational objects 82 can be preconfigured in one mode or state while other ones of the informational objects 82 can be configured in a different mode or state. For example, a surgeon may have an informational object 82 configured in the free mode and can place or position the object at a selected location in the VR world 100, such as for example in a bottom portion of a working area, and another informational object can be configured in the attached mode so that the object is always within the surgeon's field of view. Other informational objects can be disposed in the docking station 80.

Figure 6:
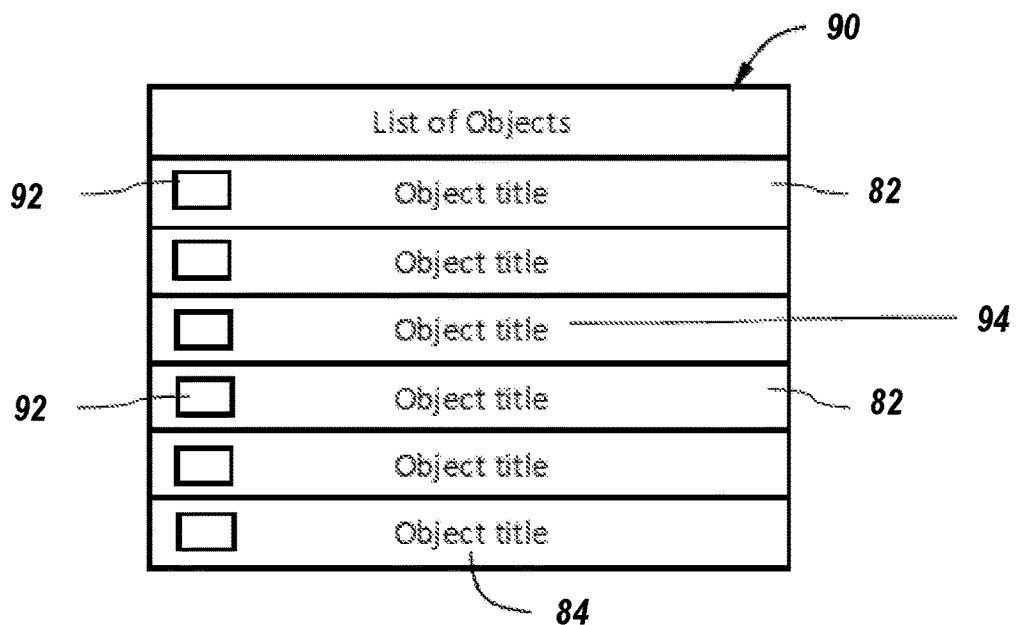
FIG. 6 is a schematic representation of a virtual reality based master list of informational objects according to the teachings of the present invention.

Additionally, the informational objects 82 can be created on demand during a surgical operation using an object list or object palette. FIGS. 5 and 6 show a schematic block diagram of the object list 90 according to the teachings of the present invention. The object list 90 is generated by the VR object generating unit 28 and can include a list of the available informational objects 82 that can be introduced into the VR world 100 and which corresponds to selected information or data generated by the system or associated devices. Each of the informational objects 82 in the object list 90 can include an optional preview 92 of the object as well as a title 84. Alternatively, instead of the preview, the list can include any suitable type of graphical representation or icon 92. The object list 90 is a master list of the informational objects 82 available to the user. Some of the informational objects set forth in the object list 90 are predefined, and some of the objects can be dynamically generated or discovered during startup or during use. According to one example, one or more informational objects associated with the video feeds generated by the cameras in the camera assembly 44 can be automatically generated by the VR object generator unit 28 and can be automatically listed in the object list 90, and can optionally be placed in the docking station 80. The list of informational objects is presented as a simple object list 90 with a small two-dimensional icon, while in other embodiments the object list 90 can be a three-dimensional object list which serves as a container of smaller three-dimensional objects that can visually represent the informational objects. In alternate embodiment, the informational object can be placed in a virtual drawer attached to the virtual surgeon workstation and generated by the VR computing unit 14. The surgeon can virtually manipulate the drawer (e.g., open or close the drawer) and can access the informational objects 82 disposed therein.

According to another practice of the present invention, the system 10 can further process for inclusion into the VR world 100 selected data 36 from any selected external data source that can be introduced to the VR computing unit 14, or can process data that is prestored in the storage unit 24. The data 36 can include for example a representation of the workstation used by the surgeon and also virtual elements that are added including virtual drawers of user interface elements, a virtual tool belt that sets forth one or more informational objects in a virtual semicircular representation, camera specific data such as zoom in and out on camera feeds, controls for medical devices, and the like. The user can interact with the virtual drawers by employing the hand controller 50 or other user input device to grab the handle of the drawer and open the drawer in the same manner one would use when opening a drawer in the real world. In some embodiments, the virtual drawer(s) may not be visible to a user in the VR world 100 until the user has translated in position across a certain threshold. Examples of a suitable threshold can include but are not limited to the side of the main body of the surgeon's workstation or other locations defined in the VR world 100.

Further, the informational objects 82 can be instantiated by selecting them and dragging them in the VR world 100. For example, the informational objects 82 can be created when the application software associated with the VR object generating unit 28 is executed by making the informational objects visible and setting or establishing the location of the objects in the virtual world to match the user selection. According to a further example, as the informational object 82 is dragged out of the object list 90 via a virtual representation of a user selection device a placeholder informational object can be used, and once the placeholder is dropped into the VR world 100 the informational object is created and replaces the placeholder. The virtual representation of the user selection device can include a virtual laser pointer beam, a reticle, or the like. The virtual user selection device is controlled by the sensing and tracking unit 16 by way of a hand controller (e.g., hand controller 50) or a head mounted controller.

The current embodiment of the present invention can be used for informational objects 82 that are expensive in computer resources such as live video feeds, but can also be used for any type of informational object. Further, instead of having the user place the informational object 82 in free mode, a soft button associated with the informational object in the object list 90 can be used to instantly place the informational object 82 in the docking station 80 or in the attached mode. The object list 90 can be configured so as to only allow one instance of a specific informational object, thus allowing the same creation process detailed above to also allow the surgeon to easily find an object which they may have lost track of. For example, if the surgeon accidentally moves an object directly behind them in the VR world 100 and can no longer view it, rather than searching for the informational object 82 the surgeon can simply drag the object out of the object list 90 once again to change the object location in the VR world 100.

When the user is in the VR world 100, they can move and place the informational objects 82 in desired locations therein using any type of controller, such as a head controller, a foot controller, or a hand controller. The hand controller can be used to move and place the informational objects in the VR world 100. The hand controller can include for example the controller 50 described herein, or can include other types of user input devices such as a joy stick, a laser pointer, a computer mouse or the like. Alternatively, a head controller such as a head mounted display can be worn by the user and can be equipped with sensors and/or eye-tracking systems which track movement of the head or the pupils of the user, respectively. When using the HMD, the user can select, move or arrange one or more informational objects in various ways, such as for example by gaze timeout in which the user stares at the object thus fixing their pupil on the object to be selected for a specified duration of time after which the object can be selected. The user may also fix their pupil on the object thus highlighting the object to be selected and then confirming the selection by pressing a button on a hand controller or pressing on a foot pedal. The gaze of the user can serve to place a reticle on the selected element, and the hand controller can be employed to select, drag, and drop the object. Further, when the informational object is selected, any suitable actuator, such as for example by a trigger button on the hand controller or a similar button on a user input device, can be used to virtually grasp the object. The informational object 82 maintains its relative position and orientation to the controller in the VR world 100 until the trigger button is released, thus placing the object at the desired location. In some embodiments, any part of the informational object can be used for selection, while in other embodiments where the informational object includes actuatable components, such as virtual buttons, sliders or other user interface controls, only a title bar can be used to move the object.

Figure 7:
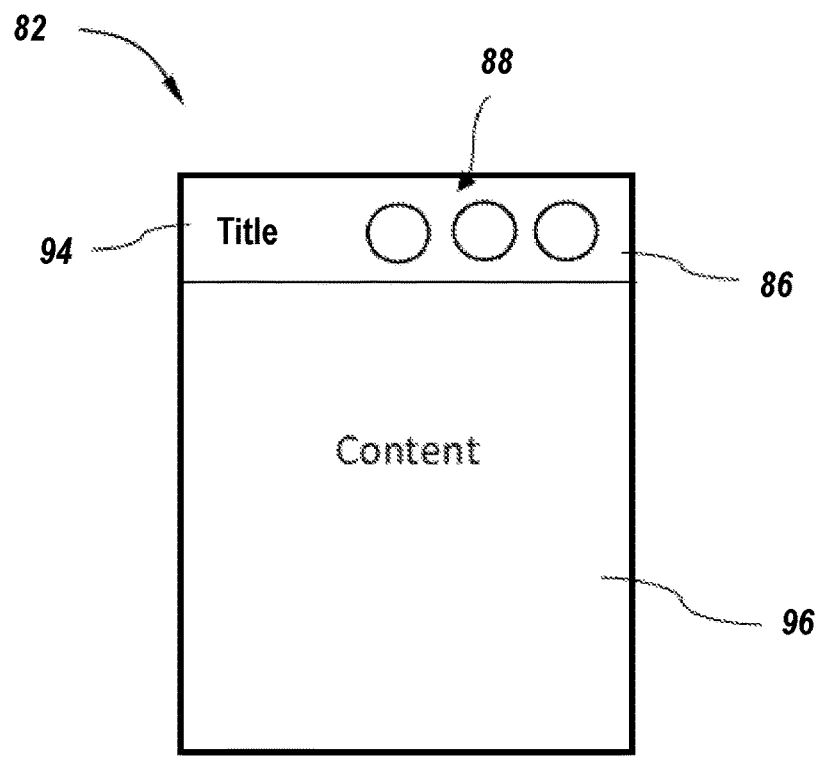
FIG. 7 is a schematic representation of the informational object according to the teachings of the present invention.

An example of a configuration of the informational object 82 suitable for use with the present invention is shown in FIG. 7. The illustrated informational object 82 includes a title bar 86 that can include the title 94 of the object as well as one or more action buttons 88 that are selectable by the user. The title 94 can preferably be indicative of the content of the informational object. The informational object 82 can also display the information or content 96 associated with the object 82. For example, if the virtual object that is generated by the VR object generator unit 28 is directed to the image data received from the camera assembly 44, then the content 96 of the object can include and display therein the image data. The title bar 86 can optionally be selectively hideable and hence placeable in an auto hide mode so that it is only visible when the object is selected by the user. According to one embodiment, when the informational object 82 is placed in the docking mode, the title bar 86 is automatically hidden. The control buttons 88 of the informational object are actuatable and allow the user to take selected actions. The actions can include for example an auto visibility button which allows the user to determine if the object is visible or not, an object mode button that allows the user to switch modes, such as between the free and attached modes, a docking station button that allows the user to move the object into a slot 84 in the docking station 80, a close button that hides the object 82 until the user creates or selects the object from the object list 90, and the like. Those of ordinary skill in the art will readily recognize that any selected number of action buttons 88 can be provided and that any selected action can be assigned to each button. The action buttons 88 can be customizable by the user or can be predefined by the system.

Figure 8:
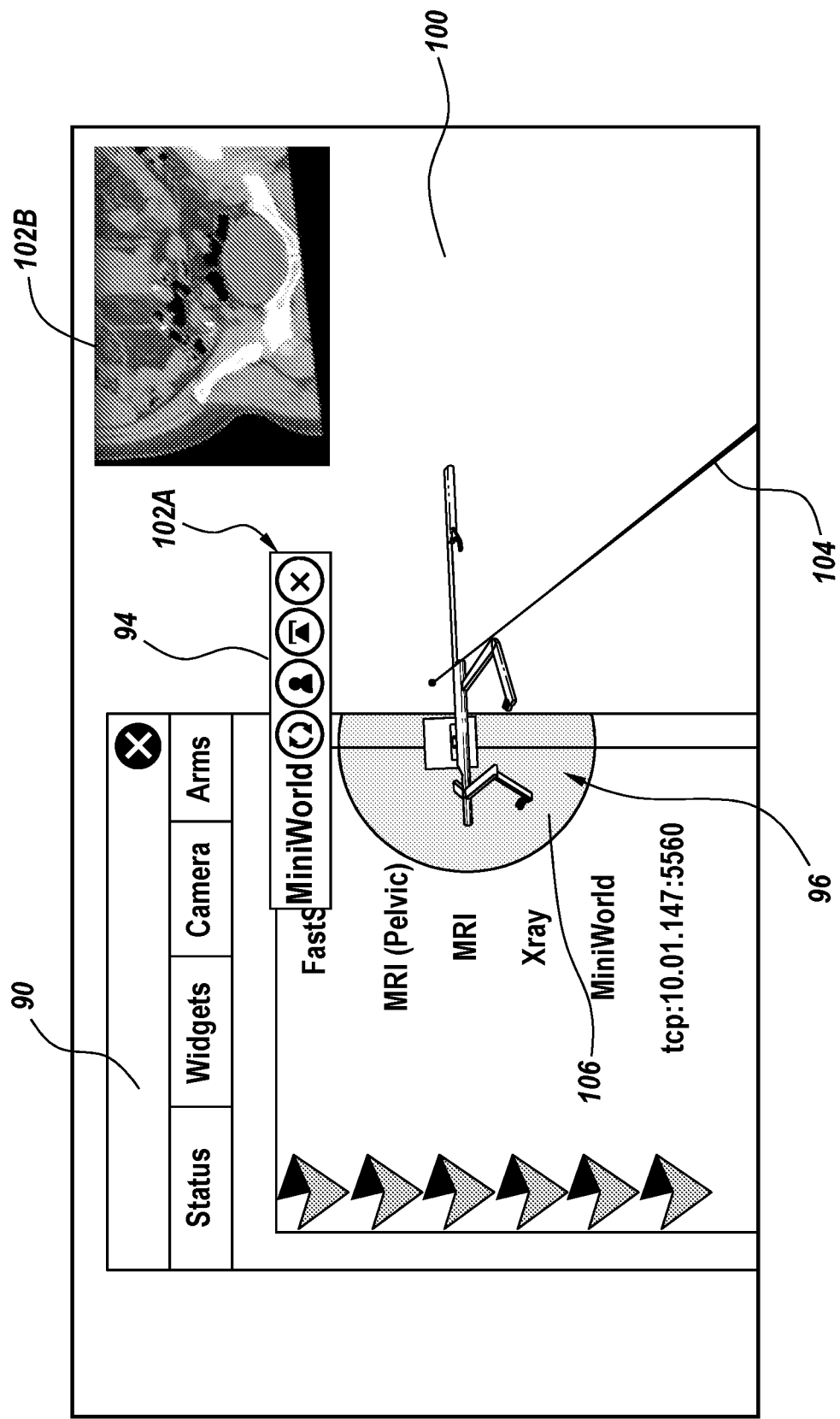
FIG. 8 is a representation of the virtual reality world generated by the system of the present invention and which displays therein an object list and associated informational objects.

The VR object generator unit 28 can generate any selected type of informational object to display, provide or emplace data generated by the system 10 or introduced to the system (e.g., data 36) from external data sources. Another example of an informational object 82 that can be generated by the unit 28 and employed by the system 10 can be a surgical system specific informational object (e.g., mini-world), as shown in FIG. 8. FIG. 8 shows the virtual reality world 100 that includes the object list 90 having a list of informational objects 82. The object list includes among the listed informational objects the surgical system informational object 102A. The informational object 102A can be selected from the object list 90 using any type of selection device, such as with a reticle (e.g., a cross-hairs or a dot style graphical element) or the illustrated virtual laser beam graphical element 104. The laser beam 104 can be pointed at and rest upon the mini-world object title in the object list 90 and the user can select the object 102A using a suitable controller, such as a hand controller. The informational object 102A can be dragged from the object list 90, and when this occurs, the information object 102A appears as shown in FIG. 7. The information object 102A includes a title bar 94 and a content region 96, which displays selected types of data, such as for example with a computer-generated virtual reality view of the surgical system 106 being used by the surgeon, that mimics the motions of the surgical system in real-time. As such, the surgical system informational object 106 can display content associated with the surgical robot, motor unit, insertion arms, trocar, robot support system (RSS), operating table, surgeon workstation, and the like. The surgical system informational object 102A allows the surgeon to visualize the surgical system, even components situated outside of the patient that are not visible to the surgical camera assembly 44 inside the body of a patient. This can even include virtual representations of a standard patient and the surgical table for reference. The virtual reality world 100 can also include additional informational objects, such as for example the MRI informational object 102B that includes MRI related information of the patient therein.

Additionally, the surgical system informational object 102A can display via the display unit 12 multiple data sets that provide a frame of reference to the surgeon. Specifically, the informational object can display images or video of one or more components of the surgical system, or the object can display a representation of one or more components of the surgical system, such as for example the robotic arms and camera assembly. These representations can be displayed within a representative virtual patient to give an even stronger point of reference to the surgeon. The display of this type of information allows the user the ability to determine a specific location and orientation of a system component, such as for example the robot arms.

According to another aspect of the present invention, the surgical system informational object 102A allows the surgeon or user to visualize transformations (e.g., translation, rotation and scale) between human movements of the hand controllers in the surgeon workstation space or reference frame, and the movement of the robotic arms 42 and associated end effectors in the virtual world 100. This auto visibility or engagement technique can be activated when the hand controllers switch from controlling the robot arms 42 to changing the transformation. The surgical system informational object 102A can be automatically activated and displayed to the user. Further, the surgical system informational object 102A can be used to visualize parts of the robot that are off camera during certain movements. For example, if the hand controllers are used to raise and lower the nominal elbow height adjustment of the robotic arms 42, the surgical system informational object 110 reference frame can visualize the elbow offset by showing the reference robot arms and the matching human arms simultaneously. This can be further augmented by showing the robot moving within a representative virtual patient. In this embodiment, the auto visibility technique can be used to make the surgical system informational object 102A automatically appear whenever the user touches the elbow adjustment toggles on the hand controllers.

The surgical system informational object 102A can also be used to visualize parts of the robotic system that are completely outside of the patient, including for example features such as support arms connected to the RSS, which individually move the robot arms and robot camera into different orientations, can be visualized as the user employs options that modifies the position of the components. For example, if the surgeon moves the RSS and in doing so the robotic system attached thereto, the current position (e.g., yaw, pitch and roll) of the system can be represented as a complete view based on data 36 introduced to the system, thus showing the current rotations at each joint of the RSS. The object 102A also allows the user to visualize the entire surgical system if desired, while concomitantly allowing the user to highlight specific components of the system.

In addition to the surgical system informational object, the system 10 of the present invention can include or employ additional informational objects that provide the user with additional information, such as for example camera related information. For example, the additional informational objects can include or provide for display live camera data of the operating room, live video output of one or more patient monitors (e.g., blood pressure, heart rate, oxygen levels and other patient vitals), live video output of any required medical device (e.g., a cautery machine or an insufflator), and/or live video output of a computer employed by a circulating operating room nurse. Additionally, in some embodiments, the informational objects can provide the user with two-dimensional and/or three-dimensional data 36 from external sources, such as for example pre-operative or live patient imagery such as X-ray scans, CT scans, MRI scans or the like. In some embodiments, the system 10 of the present invention can include a status informational object which provides a computer-generated display that shows for example the status of various aspects of the robot (e.g., robotic arms, camera clutched in status, and the like). Additionally, the object list 90 can include a clock informational object which may be used to display the current time, elapsed procedure time, and/or total robot clutch-in time. Furthermore, a patient record informational object can be found which shows pertinent patient information, such as age, weight, allergies, and the like. Additionally, a virtual ruler informational object is found in some embodiments which allows the surgeon to measure real patient anatomy with a virtual tape measure or laser distance finder. It should be noted that in additional embodiments the system 10 can include other types of informational objects which contain desired functionality or informational data requested by the user.

The surgical virtual reality user interface generating system 10 of the present invention can also employ the informational objects 82 to enable the user to engage with or clutch-in and take control of one or more components of the surgical robot system 20. By way of example, and as shown for example in FIGS. 9A and 9B, the VR object generator unit can generate a robot informational object 110 that can display information associated with, for example, the robot arms 42. The content area 96 of the object 110 can display according to one embodiment a representation of the current position 112 of the robot arms and a separate representation of the actual position 114 of the arms and hands of the user. According to one embodiment, the surgical system informational object 110 can display to the user a representation of the nominal starting position 112 of the robot arms 42 when the surgeon initially takes control, and a representation of the current position of the robot arms 114, thereby allowing the user to visualize the differences in position. In order for the user to engage with and start actuating the surgical robot system 20, the user needs to align their hands such that they match the current position and orientation of the robot arms 42 prior to the user actuating the robot. This engagement or clutch-in procedure is performed so as to prevent any unintended motion with the robot arms 42 prior to the robot following the surgeon's arm movements. When employed, the engagement procedure ensures that the robot does not move and follow the arms of the user until the user has generally matched the current position and orientation of the robot arms 42, which can include for example the angle of the graspers or end effectors of the robot arms, thus ensuring that if the robot is disengaged or clutched-out while holding an object, when it is engaged back in the same amount of force is applied in order to prevent the object in the end effectors from being dropped in the surgical site. The robot informational object 110 can provide arm engagement or clutch guidance and feedback to assist the user with properly aligning themselves with the current position of the robot arms to allow the user to engage with and actuate the robot.

Figure 9A:
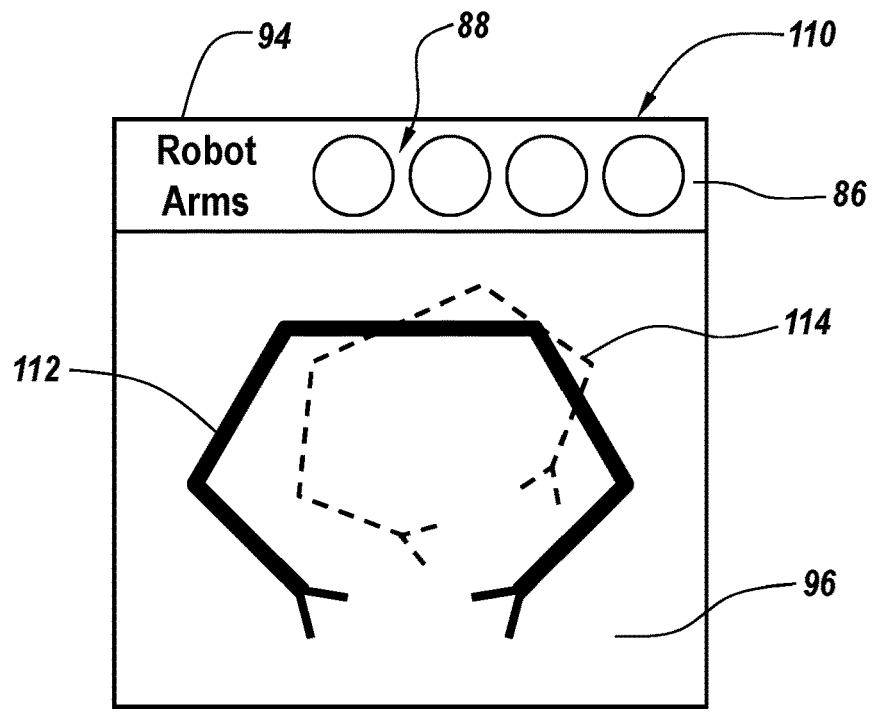
FIGS. 9A and 9B are schematic diagrams illustrating the principles of the engagement or clutch-in and the disengagement or clutch-out modes of operation according to the teachings of the present invention.
Figure 9B:
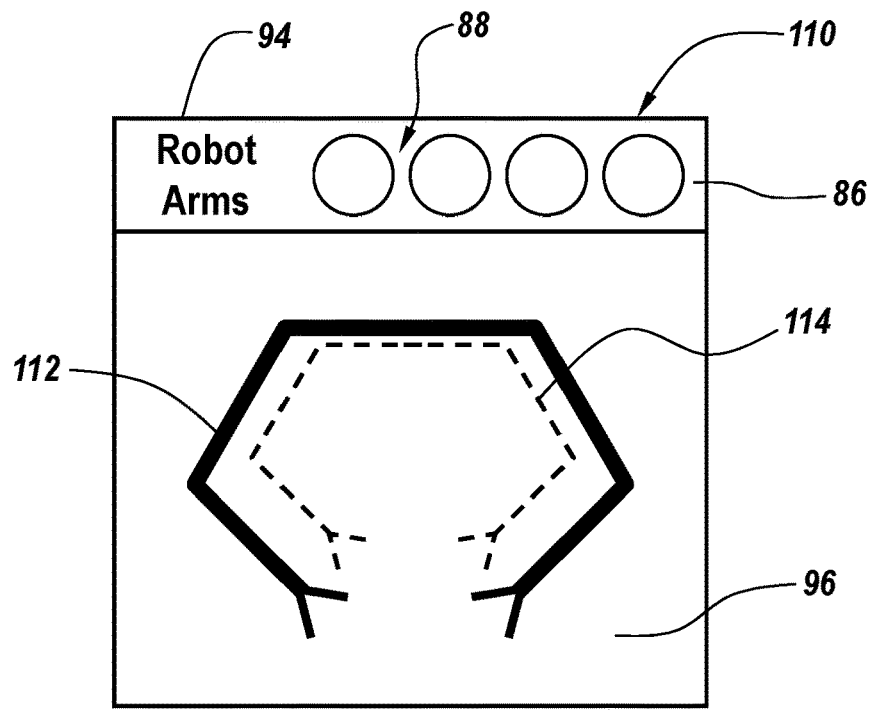

For example, as shown in FIG. 9A, the actual position of the robot arms 112 is shown in the informational object 110. The actual position of the arms of the surgeon 114 are also shown. The positions of the robot and surgeon arms can be shown or displayed using any desired visual aid or cue, and in the current example, the representation of the robot arms are shown in solid lines 112 and the representation of the surgeon arms is shown in dashed lines 114. The controllers associated with the surgeon can be placed in a disengaged or clutch-out mode where movement of the head and/or arms of the surgeon are not conveyed to the surgical robot system 20, and as such, the robot system does not move in response. The controllers can then be subsequently placed in an engaged or clutch-in mode where the movement of the surgeon is conveyed to the robot system and the robot system moves in response thereto. As such, during the engagement mode where the robot moves in response to movement of the surgeon, it is important that the surgeon's head and/or arms be aligned with the position and orientation of the robot arms and camera assembly. The informational object 110 displays positioning information to the surgeon, and when the surgeon moves, the position 114 of the arms or head of the surgeon is reflected in the content area 96, and the surgeon continues to move their arms until the arm representation 114 is aligned with the representation of the robot arms 112, FIG. 9B. When they are aligned, the surgeon can engage the controllers and then operate the robot system accordingly.

Figure 10A:
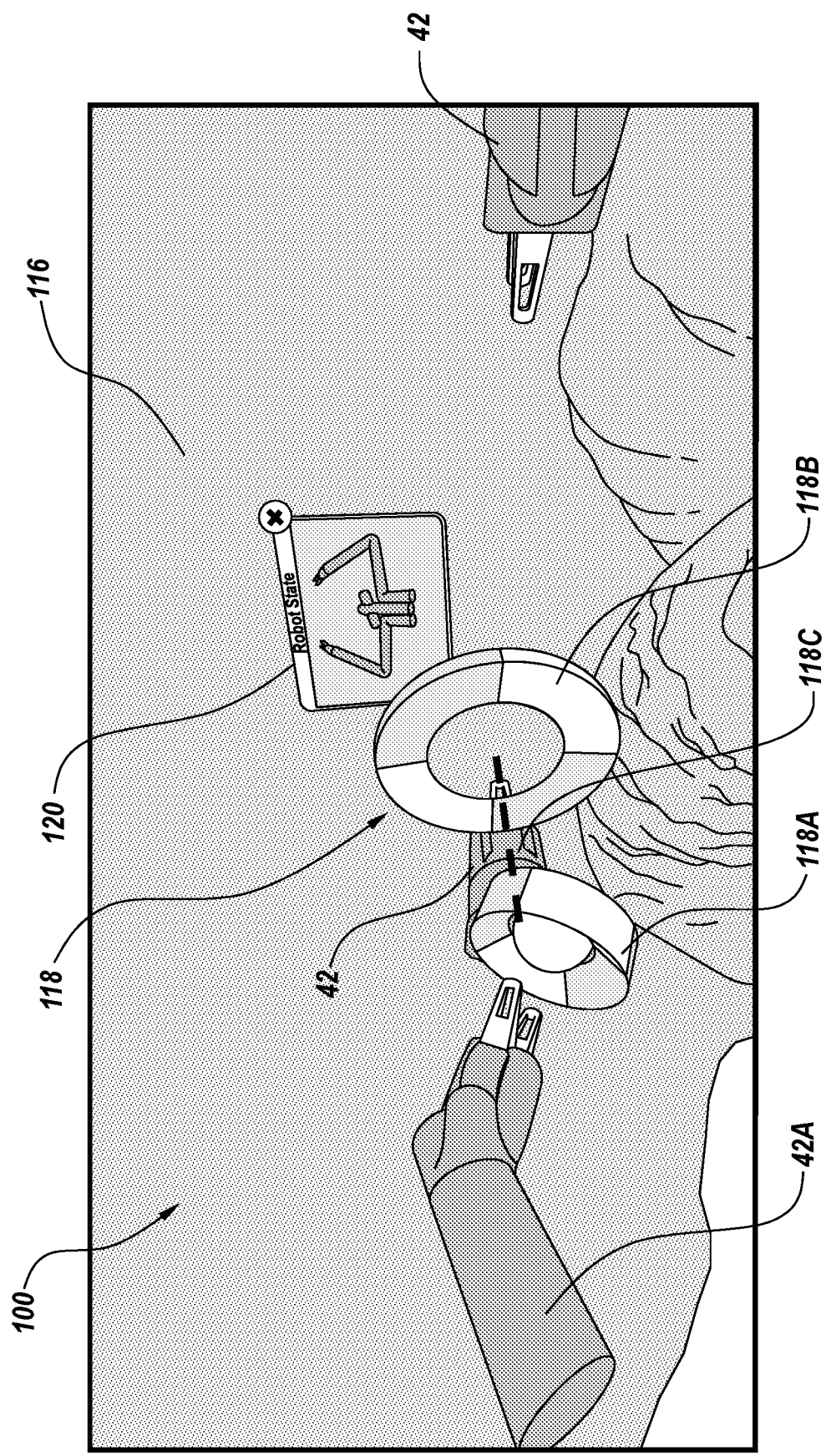
FIGS. 10A and 10B are representations of the virtual reality world generated by the system of the present invention showing the graphical elements that can be manipulated by the user when moving their arms in a selected manner so as to engage with the robot arms.
Figure 10B:
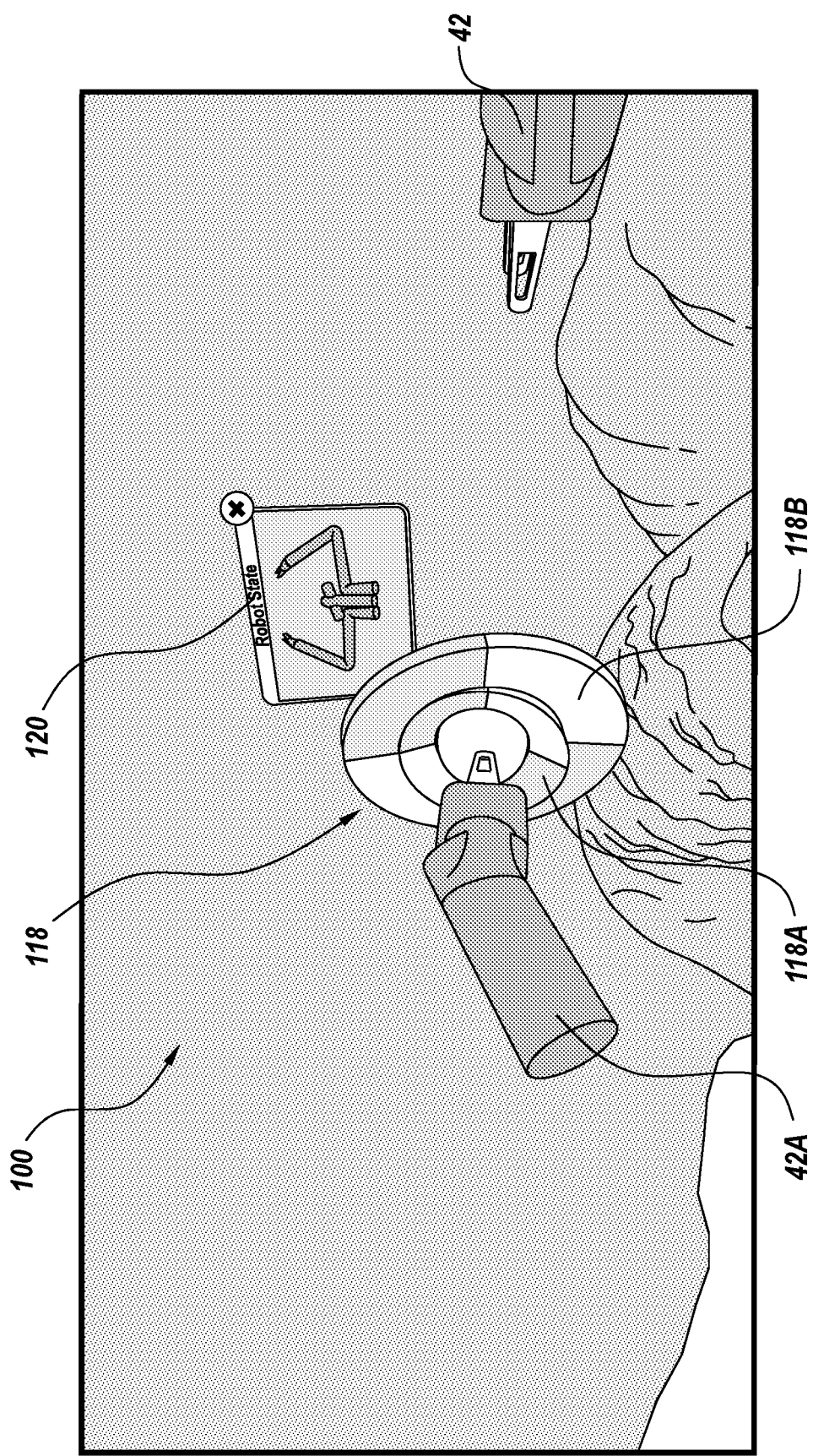

The present invention contemplates the use of any selected type of model or visual cue, such as, for example, a hand model that can be displayed in the VR world 100 as a two-dimensional or three-dimensional (3D) model of the actual physical hand controllers held by the user or attached to the workstation. In another embodiment, the hand position can be displayed in the VR world 100 as a 3-D model of human hands. In yet another embodiment, the hand model is a combination of both a 3D model of human hands and a 3D model of the hand controllers. In an alternate embodiment, the hand model can be shown as another 3D design or object which displays how the user's hands and the controllers they are holding are positioned and oriented. In still further embodiments, the hand model is configured to have a ring shape which can be positioned to match a corresponding ring which represents the position and orientation of the robot. The orientation cues can be represented by a color-coded segment on the position cue rings, as shown in FIGS. 10A and 10B.

Additionally, the grasper guidance cues can be configured as a sphere or ball that is attached to the position cue rings and the virtual robot arms. FIGS. 10A and 10B show exemplary depictions of the virtual world 100 showing the image data associated with the surgical site as captured by the camera assembly 44. The surgical site can be, for example, the inner portion of the abdominal cavity of the patient. The image data also includes data associated with the actual robot arms 42. The virtual world 100 also displays, in addition to the images of the actual robot arms 42, a virtual representation of the robot arms 42A than can be manipulated by the user via the hand controllers to move a graphical component 118A towards a cue or target graphical component 118B. The virtual world 100 also displays a robot arm informational object 120 that displays a representation of the robot arms in the content area. The informational object 120 can also have associated therewith directional arrows that allow the user to move the robot arms and the camera assembly in the yaw and pitch directions. The virtual robot arm 42A can manipulate and move the graphical component 118A towards the target graphical component 118B. Once the ring portion of the graphical component 118A is aligned with the ring portion of target graphical component 118B, the user can adjust the position of the spherical portion of the graphical component 118A towards a hole in the center region of the target graphical component 118B. The user adjusts the position of the spherical portion of graphical component 118A by adjusting the commanded angle of the grasper portion of the robot arms, typically controlled by a trigger on the hand controller 50. The user attempts to align the spherical portion of the graphical component 118A with the hole in the center region of the target graphical component 118B, and can be aided for example by other graphical elements, such as for example an alignment graphical component 118C. The graphical element 118 is positioned and oriented so as to mirror or mimic the actual position of the robot arms 42. Once the spherical portion of the graphical component 118A is aligned with and properly inserted into the hole in the center region of the target graphical component 118B, the graphical elements 118 can change colors to indicate that both the spherical portion and the ring portion of the graphical component 118A is properly aligned with the target graphical component 118B, thus indicating that both the arm grasper is properly grasping and that the arms of the surgeon are properly aligned with the position of the robot arms 42. That is, the user has properly matched the position and orientation of the robot such that from that moment on the user can properly control the robot arm. To summarize the process, as the arms of the surgeon are moved, the hand controllers can move the virtual robot arm 42A and the graphical component 118A in a corresponding manner, which indicates as shown in FIG. 10B the proper engagement position when the graphical component 118A is inserted into the center of the target graphical component 118B. When the position, orientation and grasper tolerances of the virtual robot arm 42A are all met, the robotic drive application software associated with the surgical robot system 20 indicates to the user that their arms are in a "close enough" state and after a timed delay, the user is engaged with (e.g., clutched-in) to the actual robot arms 42 and hence they are ready to actuate the robot arms. In the VR world 100, the "close enough" is indicated to the user by any selected visual cue, so as to provide feedback to the user on how the user needs to move their hands in order to match the robot's position, orientation and grasper angle. Those of ordinary skill in the art will readily recognize that in the current example, the left virtual robot arm is being manipulated. The same sequence can occur with the right virtual robot arm using similar graphical elements so as to engage or clutch-in with the right robot arm.

Furthermore, the system 10 can be configured to clutch-in or engage the robotic camera assembly 44 in addition to the robot arms 42. In order to prevent any unintentional movement of the camera assembly 44, the user aligns their head with the direction of the camera assembly 44 before engagement with the camera assembly occurs and the cameras of the assembly are actuated. In one embodiment, in the VR world 100, the user is presented with a target to look at while the user's response is measured using the any associated VR head tracking system. In another embodiment, the camera view is shown in the VR world 100, thus acting as a window into the patient's body. In this embodiment, the user can use a laser beam graphical element 104 to grab this informational object and move it in any direction and the cameras of the camera assembly 44 then move in a corresponding fashion. By moving the informational object, the user is able to move the camera so that it aligns with the user's head.

Once the user's head and camera are aligned and thus in a "close enough" state, in order to engage or clutch-in to the camera assembly 44, a proximity sensor located in the HMD worn by the user communicates with the robotic drive system to determine that user is wearing the HMD. Once this determination is made, the robotic drive system initiates the clutch-in automatically. In another embodiment, the laser pointer interface is used, with the user selecting a virtual button attached to the clutch target, while in another embodiment the user uses the laser pointer interface to select the clutch target itself in order to manually request a clutch-in from the back-end robotic drive.

According to another aspect of the present invention, the image data captured by the camera assembly 44 can be streamed over the network from the camera assembly to the VR computing unit 14. Additionally, the surgical robot system 20 can publish or broadcast additional camera related data, including for example the position, orientation, field of view and the inter-camera distance. The VR computing unit 14 can use this data to place simulated virtual scene cameras in the VR world 100 at a corresponding position and orientation and at the same inter-camera distance. The virtual scene cameras are software cameras that take images and/or live feed of the VR world and present them to the user via the screens in the HMD. In one embodiment, the image data from the left and right cameras are drawn onto quads (e.g., virtual screens) that are directly attached to the VR cameras. In these embodiments the quads are configured to move with the user's head. In another embodiment, the quads are placed in the VR world 100 based on their position and orientation as detected by the camera-drive. In the event of a camera failure, the user can select a monoscopic-view (mono-view) instead of a stereo view and use the image data of either the left camera or the right camera and have the mono-view streamed to both eyes.

Figure 11:
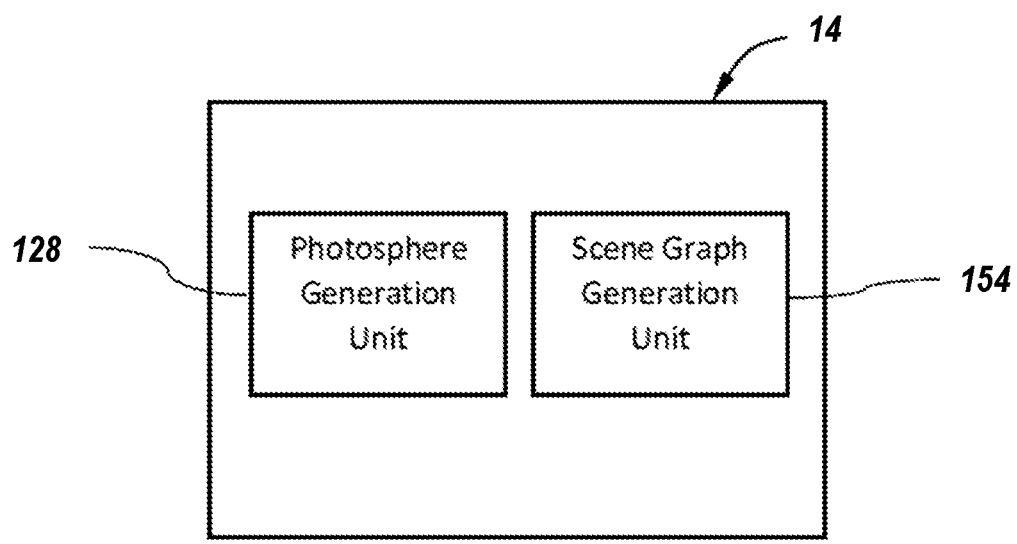
FIG. 11 is a schematic representation of the virtual reality computing unit showing a photosphere generator according to the teachings of the present invention.
Figure 12A:
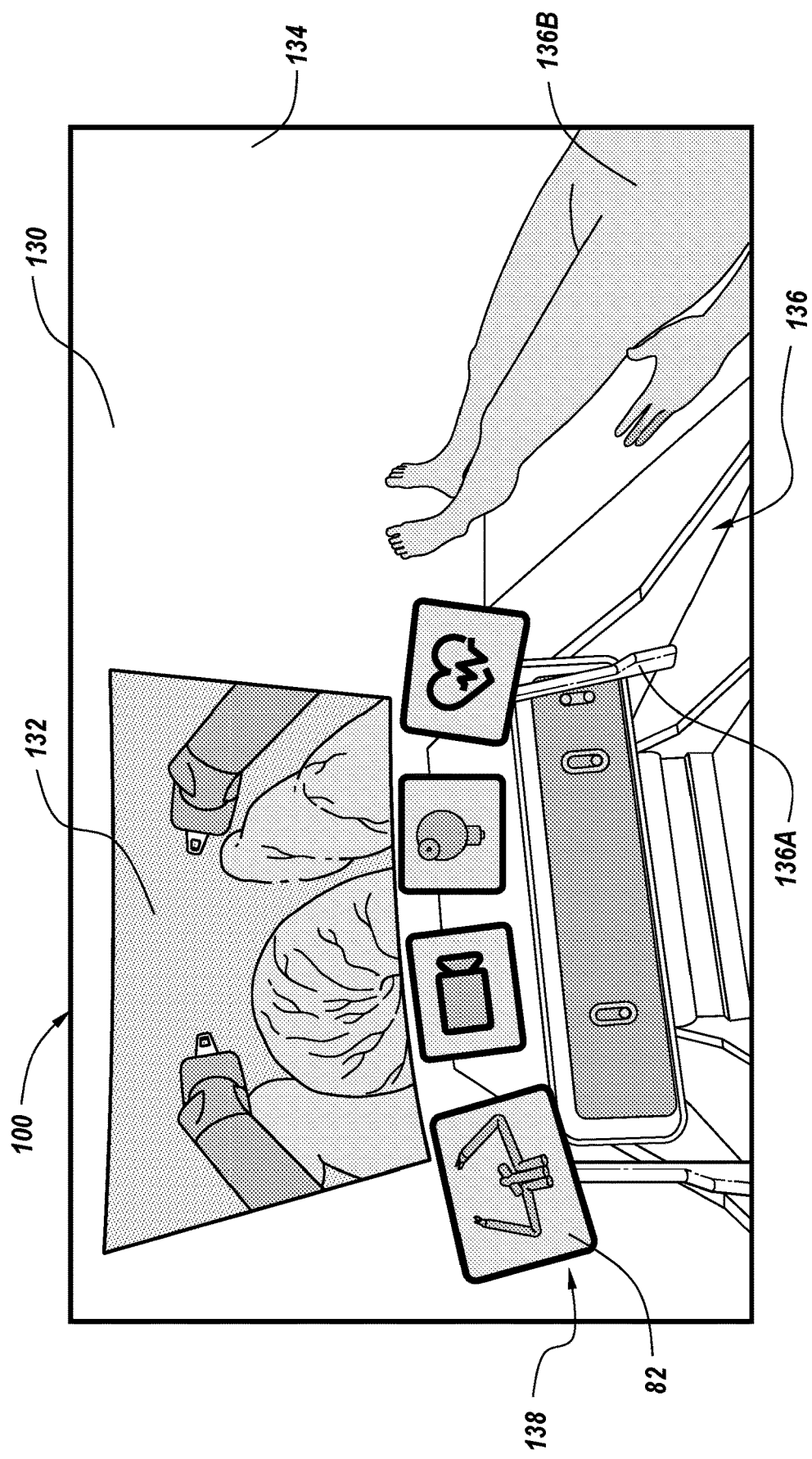
FIG. 12A is a representation of the virtual world employing a photosphere according to the teachings of the present invention.
Figure 12B:
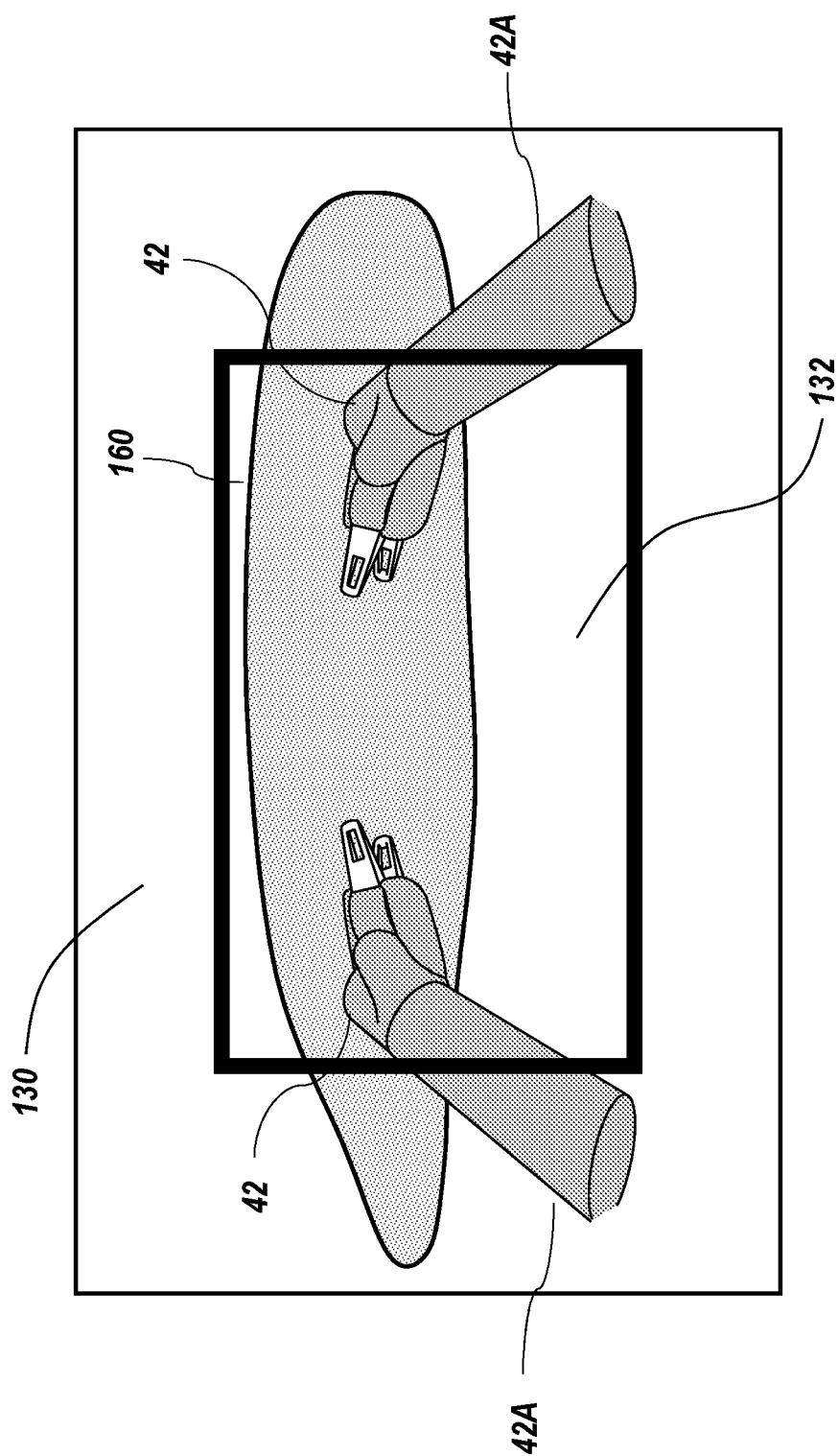
FIG. 12B is another representation of the photosphere according to the teachings of the present invention.
Figure 13:
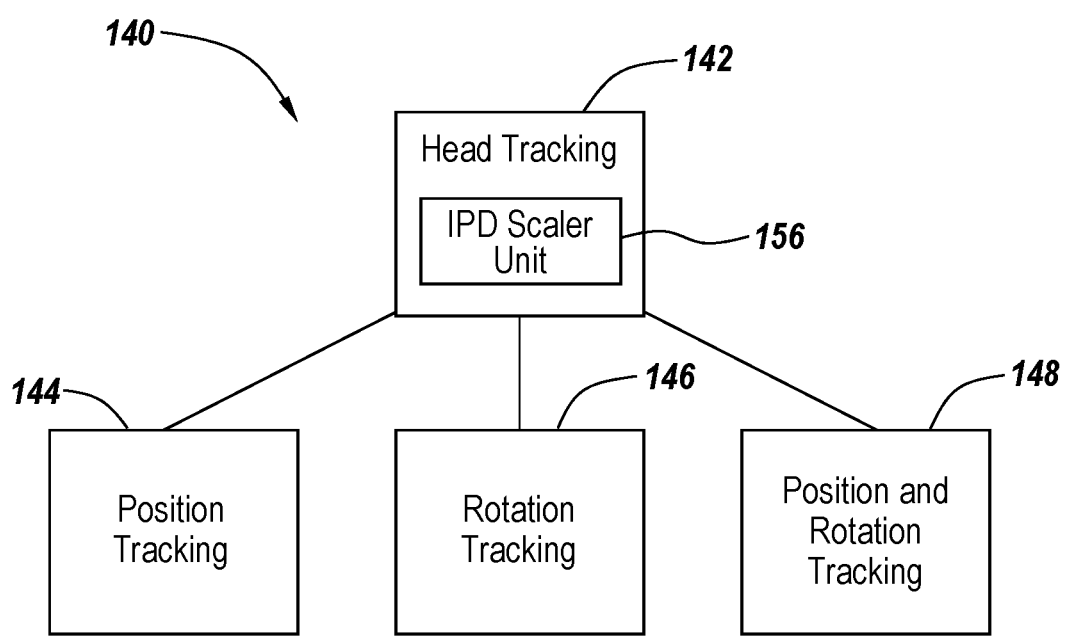
FIG. 13 is a schematic representation of a scene graph according to the teachings of the present invention.

The surgical virtual reality user interface generating system 10 of the present invention is also configured to generate data from the surgical robot system 20 and to generate objects for display in the VR world 100. The present invention is specifically configured to capture image data from the camera assembly 44 and to generate via a photosphere generation unit a photosphere of the entire environment surrounding the camera assembly. As shown in FIGS. 11-13, the VR computing unit 14 can include a photosphere generation unit 128 for generating the photosphere 130. Those of ordinary skill in the art will readily recognize that the photosphere generation unit 128 can also form part of the computing unit 18. The photosphere 130 as is known can include a number of interactive wide-angle panoramic images generally encompassing if desired a 360-degree circle or a spherical view relative to the user. The photosphere 130 can form a complete scene from a plurality of images from the image data, as viewed when rotating about a single central point or position. If formed from multiple photos or images, the images can be stitched together according to known conventional techniques. Alternatively, the photosphere 130 can be formed from a partial or complete virtual reality image that is generated by the VR computing unit 14 or from a composite of photography and computer generated objects. This is similar to taking a panorama photograph on most modern smart devices but is not limited to rotating the camera about one axis and instead about two axes such that a sphere of images gets stitched together for each of the two cameras in the stereoscopic camera.

According to the present invention, the photosphere 130 can be generated via the photosphere generation unit 128 and can be configured to render to a cube map that is used as the background of the VR world 100. The system of the present invention can also employ a virtual reality (VR) camera unit 38 for generating one or more virtual reality (VR) cameras for use or emplacement in the VR world 100. The system can also employ a scene graph generation unit 154 for generating a scene graph 140 having one or more VR cameras as a peer or child of the nodes which have the main virtual cameras, and which render the images for the head-mounted display. This ensures that the VR camera always renders the same views that the user wearing the head-mounted display sees to the cube map. In one embodiment, a single VR camera can be used and in another embodiment separate left and right eye VR cameras can be employed to render onto separate left and right eye cube maps to provide a stereo view. The FOV setting of the VR camera can self-configure itself to the FOV published by the camera assembly 44. In addition to providing a contextual background for the live camera views or image data, the cube map can be used to generate dynamic reflections on virtual objects. This effect allows reflective surfaces on virtual objects to pick up reflections from the cube map, making these objects appear to the user as if they're actually reflecting the real world environment.

Further, the photosphere 130 is typically only valid in the location in which it was captured. Once the camera assembly 44 is moved, the images the camera assembly captures no longer line up with the images in the photosphere 130. When the camera or the robot support system (RSS) that is holding the camera is moved, the updated position can be published on the network as inter-process communication (IPC) messages. The photosphere implementation can then completely erase the cube map, setting all the pixels to black, in order to make sure that no old image data remains in the photosphere. In one implementation, the system can perform an autoscan each time the camera is moved to allow a complete new photosphere to be constructed and ready for the user.

According to the teachings of the present invention, the orientation of the camera assembly 44 can be driven by the orientation of the head mounted display (HMD) such that the cameras of the camera assembly 44 are positioned and oriented in the direction where the person wearing the HMD is looking and the images from the cameras are shown within the display portion of the HMD. This present invention can be utilized for example when the camera assembly 44 has a smaller field of view (FOV) than the field of view of the HMD on which it is shown. Outside of the FOV of the camera would be displayed the generated photosphere. The generated photosphere provides historical information that has not been updated since last entering the field of view of the camera assembly. As such, the photosphere 130 provides environmental context and effectively extends the peripheral vision of the user. According to one practice, the movement of the HMD can serve to update the photosphere 130 with additional image or video data. The historical, non-live nature of the photosphere can be indicated by adjusting the color or hue of the image. In one embodiment, the photosphere is shown in grayscale.

The system of the present invention can also employ an autoscan mode where the control unit 26 generates control signals that are received by the camera assembly 44, and where the cameras autonomously rotate through the cameras entire range of motion to capture images of the work space or surgical site within the patient. The cameras of the camera assembly 44 generate image data that can be conveyed to the photosphere generation unit 128 for generating the photosphere 130 or for updating the image data in the photosphere 130. The photosphere 130 can thus include image data from the cameras. After the photosphere 130 is populated with the image data, the photosphere generation unit 128 can continuously or periodically update the image data in the photosphere with image data received from the cameras. The autoscan mode can also be configured to only scan areas required to fill in the parts of the FOV of the HMD that are not covered by the camera FOV based on the current direction of the user's gaze. During the autoscan mode, it appears to the user wearing the HMD as if the camera stops moving along with their head movements. As such, the user is free to look at any part of the photosphere 130 via the HMD or display unit 12 and as the user views the image data in the photosphere 130 they can observe the image data in the photosphere being updated (e.g., painted) as the camera assembly 44 is swept across its range of motion. In one embodiment, the autoscan mode can be employed to capture the images from the stereoscopic cameras of the camera assembly 44 and can be used to create a rendering of the procedure site, thus allowing the user to obtain images of the site.

The system of the present invention can also be used to support multiple observers of the robotic camera assembly 44 as well as post-surgical review of image data generated by the camera assembly. In both of those instances, simply playing back the recorded image data into the HMD is typically uncomfortable for the observer because the motion of the FOV of the camera of the images typically does not match the motion of the head of the observer while watching. To the observer, the images appear to rotate about the surgical field but only based upon what the user is doing and not at all under the control of the observer. The conflict between what the observer sees with their eyes (i.e., panning camera images) and what their vestibular system experiences (e.g. no head movement) may cause simulator discomfort, dizziness, or sickness. However, in the present invention, the observer can watch the images of the photosphere 130, and thereby be presented with a 360 degree view in which the observer can freely move their head and observe in any direction and not be made uncomfortable by a mismatch between observed head motion and their actual head motion. According to one practice, only a portion of the photosphere 130 represents the live image data from the camera assembly 44, and the live image data can be incorporated into the photosphere 130 in the context of all the other images that have been recorded. For example, as shown in FIG. 12B, the generated photosphere 130 includes the a virtual representation of the robot arms 42A, 42A that are emplaced into the VR world of the photosphere. A live camera feed or window is presented as part of the image data field 132 and can include the video images of the actual robot arms 42, 42 performing surgery on a human organ 160. The organ can be presented as part of the live video feed as well as part of the photosphere 130.

The illustrated photosphere generation unit 128 can also be configured to differentiate the live image data captured by the camera assembly 44 from older image data in the photosphere 130. According to one practice, the system 10 provides a seamless photosphere 130 with as few image artifacts as possible. One approach is to employ standard image blending techniques such as dissolve, multiply or dodge and burn techniques. These techniques can help to soften the hard edges of each image rendered onto the photosphere as well as the edges of the current images against the photosphere. Another technique is to change the frequency at which the images are rendered by the VR camera and applied to the photosphere. Slower rendering means the photosphere data has fewer edges to blend and shows slightly older imagery whereas faster rendering means that there are more individual edges to blend with lower latency. In other embodiments, smart blending or image stitching techniques that can understand the scene and the objects in it can improve the smoothness and quality of the composite image. For example, if the system can understand that an object in one image is the same as an object in a second image it can make sure that the contours of the object smoothly and continuously mesh. This technique can employ artificial intelligence, machine learning and computer vision to these ends.

The present invention can also clearly delineate which images are "live" and which are older and form part of the photosphere 130. Older imagery can potentially be a safety concern, for example in a surgical system, if the patient starts bleeding in an area that is not being imaged live and was only visualized as a part of the photosphere 130. In this example, the surgeon does not know the current status of the bleed until they move their head to drive the camera back to that area to get updated imagery. In the context of extra observers or post-surgical review, it is desirable to determine which direction the surgeon is looking. Several techniques can be applied to make this easier to discern. In one embodiment, the resolution of the cube map texture can be lowered so that the pixel density of the areas of the HMD's FOV that are shown as part of the photosphere 130 are significantly less than the pixel density of the camera quads onto which the live imagery is being mapped. This may give the photosphere 130 a blocky, pixelated appearance which can be softened by applying a blurring filter to the cube map. In another embodiment, the brightness of the cube map texture is reduced so that the photosphere 130 appears darker and the live-updated camera quads appear significantly brighter. In still another embodiment, a frame object is placed around the camera quads so there's a visible border between the live data and the photosphere 130. An example of this technique is clearly shown for example in FIGS. 12A and 12B. The photosphere 130 generated by the photosphere generation unit 128 employs the image data generated by the camera assembly. The photosphere 130 includes an image data field 132 that is differentiated in known ways from the remainder of the photosphere 134 and can present live image data of the surgical site that is captured by the camera assembly. The remainder portions of the photosphere can be differentiated in visual ways from the image data field, such as for example by blacking out the remainder portions of the photosphere or at least the portions of the photosphere immediately adjacent to the image data field 132. The photosphere 130 can also be configured to display a virtual representation of the surgical system and the surgeon work area or station 136, which includes virtual representations of the hand controllers 136A, for ease of reference. In one embodiment, a virtual representation of the patient 136B can also be included. The virtual world 100 can also include, if desired, a second type of docking station configured in the form of a tool belt style docking station 138. The tool belt docking station 138 can include if desired a plurality of informational objects 82. The tool belt docking station can be located in the virtual reality world 100 around the waist area of the user, and hence can be disposed within the view of the user when they look in a downward direction or alternately out of view when they look in upward direction.

In yet another embodiment designed especially for post-surgical and remote viewing, directional indicators such as arrows are placed in front of the user. These indicators guide the user's gaze towards the camera quads and the current direction in which the robotic camera is pointed. These are added as objects in the scene graph 140 which can either be attached to the VR cameras (so they're effectively attached to the user's head) or they can be placed at fixed positions in the virtual reality world 100. The objects can be setup so that they're always on or only shown when the HMD is moving by more than a specified threshold. The latter mode allows the user to look around and focus on something without the arrow getting in the way and then as they look around to try to find their way back to the "live" camera quads the arrows will appear to assist.

The user who is directly in control of the surgical robot system 20 is known here as the primary operator, user or surgeon, and any other observers are known here as third person observers. The third person observers can either observe a live surgical session or replay a previously recorded session for after action review. The primary observers can either be participating on a local area network or remotely via a wide area network. They can connect to both the video streams and the inter-process communication (IPC) messages and associated data. Although remote observers may be wearing an HMD they will not be using it to control the robotic camera. Therefore their camera quads will need to be driven by the IPC messages which describe the commanded position of the robotic camera. This will cause the live images coming from the camera to appear on the quads which are positioned based on where the primary operator is pointing the robotic camera.

Further, post-surgical review can be achieved by recording timestamps in both the recording of the video stream data as well as the IPC data. In one embodiment, the timestamp is encoded into the metadata of the video stream and the IPC data is written to disk with timestamps in JSON format. The playback application can simultaneously publish both the video and IPC data and maintain the correlated timestamps between the two data sets. After action review is possible in the same VR application that live observers use; the only difference is that the data is coming from the playback application instead of a live session.

There are multiple scales of objects that the VR computing unit 14, such as by employing the optional VR camera unit 38, can be used to render and present to the user via the HMD. For example, there are objects that are rendered within the VR world 100 at the scale of the robot and there can additionally be objects rendered at the scale of the human. In this example, as is standard practice with most virtual reality applications today, the user can be presented with a virtual representation of the hand controllers and objects with which their hand controllers can interact. From the perspective of the user, the hand controllers and the objects that they interact with appear to be at one to one scale with the real world. In that same virtual world there may exist a rendering of a virtual representation of the robotic arms at a scale that is different than that of the apparent scale of the real world from the perspective of the user. Because these two sets of objects are at different scales it can make it difficult for them to interact with each other or be presented to a user in a fashion that makes them appear at the same scale. In order to solve this problem, one set of objects is scaled up or down by the appropriate amount to make it match the scale of the other set of object. To that end, the system of the present invention is also configured to allow the virtual cameras used to generate the views for each eye within the head-mounted display (HMD) to employ the same inter-camera distance (ICD) as the stereoscopic robotic camera assembly 44. Even when the ICD is substantially different from the user's inter-pupillary distance (IPD), the present invention maintains proper scaling of both objects drawn at robot scale and those drawn at human scale by estimating the scaling factor to be equal to the ratio of the IPD of the user (in distance units) to the ICD of the camera assembly (in the same distance units). This scaling factor is then applied to either scale up the objects at robot scale or the inverse of the scaling factor is used to scale down the objects at human scale. This allows the system to switch between showing objects at robot scale and showing objects at human scale and even showing objects at both scales simultaneously, and thus in any case all objects appear to the user at human scale. For example, if the IPD of the user is 65 mm and the ICD of the camera is 13 mm, the scaling factor can be estimated to be 5 mm by dividing the IPD by the ICD (IPD/ICD), which can then be used to scale up a virtual representation of the robot arms at robot scale object by five times, and present them to the user via the HMD so that they appear to be at human scale. Other measurements of user anatomy if available can be utilized for the scaling factor estimate. For example, the user can hold their arm straight out and the distance between the hand controller and the HMD can be taken as an estimate of user arm length. The scaling factor can then be estimated to be the ratio of the estimated length of the user's arm (in distance units) to the known length of the robot arm (in the same distance units). This scaling can also be applied to the head tracking so that as the HMD is tracked in human scale and those movements can be scaled down and applied to the virtual camera at robot scale.

The present invention also addresses robotic camera assemblies 44 which typically have fewer degrees of freedom (DOF) than a human wearing a head mounted display. For Example, if the camera assembly 44 can only rotate in the yaw and pitch directions (e.g., two degrees of freedom), this may present a problem because human head movement tracked in the VR world 100 can also rotate, in addition to the yaw and pitch directions, in the roll and translate directions (e.g., x, y, z) for a total of six DOF. The camera assembly 44 can also send over the system network data directed to selected types of parameters, including for example the current position & orientation (e.g., pose) of the cameras in the camera assembly 44, the ICD, and the field of view (FOV). The VR computing unit 14 can then configure the VR world 100 to align for example the virtual cameras therein. Further, as is known in the art, the VR world 100 can be represented by a series of data structures that are hierarchically organized as part of a scene graph. The scene graph arranges the logical and often spatial representation of a virtual reality graphical scene, and can be represented by a series of nodes in a graph or tree structure. An example of a tree type scene graph representative of the VR world 100 is shown in FIG. 13. The illustrated scene graph 140 can be generated as noted by the scene graph generation unit 154 and can include a parent node 142 that is directed to the head tracking sensors associated with the display unit 12, and specifically the head mounted display. The scene graph 140 is configured such that all child nodes 144, 146, 148 are subject to the properties of the parent node 142. The head tracking parent node 142 receives tracking data from the camera assembly 44 via the VR object generator unit 28 and the VR computing unit 14 and applies the data, typically representative of the position of the HMD, to the child node. The scene graph 140 by way of a simple example can include a child node 144 that is directed to only position tracking data, a child node 146 that is directed to only rotation tracking data, and a child node 148 that is directed to position and rotation tracking data.

In the VR world 100, the virtual cameras generated by the virtual camera unit 38, FIG. 1, can be configured to directly track the position of the HMD. A properly implemented neck model is important to user comfort where the pose of the virtual camera matches the eyes of the user as the user tilts their head. If the IPD is scaled down but the head tracking is not adjusted, it appears to the user as if their head is traveling through a much greater arc as they tilt their head. To get this ratio correct and to reduce or eliminate this occurrence, the scene graph generating unit 154 can generate a scene graph 140 that includes an IPD scaler unit 156 that can scale the position and rotation data received from the HMD so that the data associated with the HMD is at robot scale instead of at human scale. Each of the child nodes in the scene graph 140 is also subject to the constraints of the IPD scaler unit 156, with the invert scale parameter enabled. This allows objects positioned beneath these nodes (e.g., child nodes) to appear at their default scale and not inherit any scaling intended to correct the neck model. In the default configuration, the IPD scaler unit 156 can generate and apply a scaling factor to scale human scale objects to robot scale. The IPD scaler unit 156 can also be configured to perform inverse scaling, which allows the child nodes to reverse the scaling applied by the IPD scaler unit of the parent node. The scaling can also optionally be performed by the VR camera unit 38.

Further, in the case of the surgical robot system 20, the ICD is typically quite small compared with a normal human IPD, because the robot needs to fit inside the patient. The IPD scaler unit 156 can address this discrepancy by reading the ICD value published onto the network by the camera assembly 44. The scaler unit 156 can also read the IPD data of the HMD as published by the associated virtual reality API (e.g. OpenVR, OpenXR, and the like) and apply that to the position of the headset in order to determine the distance between the virtual scene cameras, known here as the virtual camera ICD. The scaling factor that can be applied to the parent node and generated by the IPD scaler unit 156 is determined by dividing the robotic camera ICD by the virtual camera ICD.

The image data generated by the robotic camera assembly 44 can be used as textures on one or more quads of the head mounted display (i.e. rendered onto the quads). In the HMD, each eye display has at least one quad associated therewith. The FOV value broadcast by the camera assembly 44, one for each eye of the HMD, can be positioned & oriented using two different techniques. Both techniques require the camera assembly 44 to publish the FOV values. The FOV value allows the size of the quads and/or distance between the quads and the virtual cameras to be adjusted such that they occupy the same FOV in the virtual would as they do in the real world.

According to one practice, the size and position of the quads in the HMD can be configured to always appear directly in front of the virtual cameras and therefore in front of the user when viewed through the HMD, and can be further configured to maintain the relative position of the quads so as to not rotate in selected manners that the real camera cannot.

According to another practice, in the system of the present invention the cameras in the camera assembly 44 have position sensors that detect the pose of the camera in all the degrees of freedom (DOFs) in which the camera can be moved and rotated by the user. These values are sent via the network from the camera to the VR application and applied to the "Camera Driven Camera Quads" node. This enables the quads to be shown at the position that corresponds to the real world pose of the camera. This can be an advantage when the robotic camera moves slower than the human's head (as tracked by the HMD). The quads and thus the camera images can be shown in the virtual scene where they are as reported by the camera such that if the human head moves more quickly than the camera assembly is able to move then the quad positions follow the movement of the camera assembly and eventually match the pose of the user after their head stops moving. In some robotic camera systems the sensed pose data may come in at a much faster rate and/or with lower latency than the video feeds. In these cases the application of the sensed data to the "Camera Driven Camera Quads" node can be delayed via an asynchronous await function (or some equivalent) to allow the sensed data to correlate better with where the video feed images are shown.

According to a simplified example, a surgical site can be observed with the camera assembly that is actuated to match the pose (e.g., yaw, pitch and roll) of the user wearing the HMD. The camera assembly 44 can include a left camera module and a right camera module separated by a distance known as the inter-camera distance (ICD). Each camera module consists of at least a lens or lens stack, an image sensor and a housing to hold everything in the appropriate locations. Each image sensor is exposed to light via the lens or lens stack and produces an image that is then sent to the system 10 to be displayed in the display unit 12. The entire dimensions of the image sensor may be exposed to light or only a portion or sub-section of the image sensor may be exposed to light. The part of the image sensor used to generate the image is known as the active portion of the sensor. Each camera module is specified to have a known set of parameters such as for example focal length, field of view (FOV) and sensor size, and should have low distortion and aberration. The FOV of the cameras can be measured as a diagonal FOV or separately as horizontal or vertical FOV with an associated aspect ratio (e.g., ratio of height to width of image).

The system can be configured to generate via the VR computing unit 14 the virtual world 100 that can be displayed on the quads of the HMD, and hence viewable therethrough. The virtual world can include at least one virtual camera and one finite plane surface per eye (e.g., a quad). According to one practice, there is one quad visible only to the right virtual camera and another quad visible only to the left virtual camera. Each virtual camera functions similar to a real camera in the real world in that it creates an image based upon the virtual scene presented to the camera. The image collected by the left virtual camera is observed by the user's left eye via the optics in the HMD. The image collected by the right virtual camera is observed by the user's right eye via the optics in the HMD. The quads are positioned such that they are perpendicular to the visual axis of each virtual camera such that the user can observe them to have height and width but cannot observe their depth. Upon the right quad is displayed the image from the right camera module of the camera. Upon the left quad is displayed the image from the left camera module of the camera. The virtual dimensions of the quads are such that the ratio of height to width of each quad is equal to the ratio of the height (in pixels) to the width (in pixels) of the desired image from the respective camera module.

In order to create a comfortable and to-scale representation of the scene for the user to observe the surgical scene through the HMD, the known parameters of the camera are taken into consideration when designing the virtual world 100. The field of view of each camera module is a function of the dimensions of the active portion of the image sensor and the focal length. The perceived field of view per eye through the HMD is a function of the dimensions of the quad and the depth that it is placed from its respective virtual camera and several dimensional ratios derived from those values. The ratio of the width of the active portion of the image sensor (in mms) to the focal length (f) of the camera module (in mms) should be equal to the ratio of the width of the quad (in distance units) to the depth that the quad is placed from its respective virtual camera (in the same distance units). Additionally, the ratio of the height of the active portion of the sensor (mms) to the focal length (f) of the camera module (mms) should be equal to the ratio of the height of the quad (in distance units) to the depth that the quad is placed from its respective virtual camera (in the same distance units). The dimensional ratios can be characterized as set forth in the following formulas.

$$\text{(width of active portion of sensor)}/f = \text{(width of quad)}/\text{(depth of quad)} \quad (1)$$

and, $$\text{(height of active sensor portion)}/f = \text{(height of quad)}/\text{(depth of quad)} \quad (2)$$

Maintaining the ratios in formulas (1) and (2) ensures that the horizontal and vertical fields of view of the image from each camera module is equal to the perceived horizontal and vertical fields of view per eye within the HMD, respectively. This can alternatively be accomplished by the following equations holding true.

$$\text{(height of active sensor region)}/\text{(width of active sensor region)} = \text{(height of quad)}/\text{(width of quad)} \quad (3)$$

and either one of equations (4) and (5), as follows:

$$\text{Depth of Quad} = \text{(Height of Quad)}/(2*\tan(\tfrac{1}{2}*\text{vertical FOV})) \quad (4)$$

or, $$\text{Depth of Quad} = \text{(Width of Quad)}/(2*\tan(\tfrac{1}{2}*\text{horizontal FOV})) \quad (5)$$

According to one practice, the aspect ratio of the active portion of each of the left and right camera modules is duplicated respectively on the left and right quads viewed through the HMD following the above equations. As such, each quad can be flat and rectangular and the size of each is arbitrarily set. The depth of each quad associated with a corresponding virtual camera is set and calculated using one or more of the above formulas.

According to another practice, the quads can include a cylindrically curved rectangular surface (e.g., similar to a curved television) and the angular measurement of the corresponding FOV, either vertical or horizontal, can be used to define the angular cross-section of the cylindrical section that defines the quad. The virtual camera can be placed at the center of the cylindrical section. The quads can consist of a surface of arbitrary shape and curvature, such as a portion of a sphere. The curvature of the quads can be used to create certain perceived effects on the image, such as lens distortion correction or exaggeration. The shape of the quad can affect the users comfort while moving his or her head.

If there is a mismatch between the dimensional ratios or of the field of views between those of the camera modules and those perceived in the HMD, there are several negative things that can occur. For example, if the perceived field of view is larger than the actual field of view of the camera module, the user may likely feel that the world is too large or zoomed in. Additionally, in that configuration, when the user moves his or her head the perceived angular rate of motion may be different than the actual angular rate of motion of the user's head. This discrepancy in rate can cause discomfort or nausea to the user.

Additionally, the ratio of the ICD (mm) to the desired working depth (mm) in the surgical scene should be equal to the ratio of the IPD (mm) of the user's eyes to the desired working depth (mm) for the user. In one embodiment, the desired working depth in the surgical scene is equal to the length of the robotic arms and the desired working depth for the user is equal to the length of the user's or a typical user's arm. In another embodiment, the desired working depth in the surgical scene is equal to a set fraction of the length of the robotic arms and the desired working depth for the user is equal to that same set fraction of the length of the user's or a typical user's arm. Mismatches in this ratio result in the user experiencing a varying degree or strength of depth perception as a result of varying amounts of image disparity (binocular parallax). For example, if the ICD is larger than it should be based upon the ratios, the user will feel an unnaturally strong sense of depth (from disparity). Additionally, as the user brings an object close to the cameras the distance at which the stereoscopic images diverge (similar to one going cross-eyed when the brain cannot construct a 3D view of the scene and the user experiences double vision) will become longer meaning that the user cannot comfortably work as close to the cameras as they could with a smaller ICD. Conversely, if the ICD is smaller than it should be based upon the ratios, the user will feel an unnaturally weak sense of depth (from disparity). The smaller the ICD the less depth perception the user can sense from disparity. At a theoretical ICD of 0 mm the user would experience no depth perception from disparity and it would be similar to the user observing the scene via a standard 2D television. An important thing to note is that a human uses dozens of cues that give him or her a sense of depth, only one of which is disparity. Other cues include accommodation, convergence, monocular parallax, retinal image size, linear perspective, gradients, etc.

Aspects of the subject matter described herein can be implemented in digital electronic circuitry, or in computer software, firmware, or hardware, or a combination of the foregoing, including the structural components disclosed in this specification and structural equivalents thereof. Further, aspects of the subject matter described herein can be implemented using one or more computer program products, such as one or more computer programs tangibly embodied in an information carrier (e.g., in a machine readable storage device), or embodied in a propagated signal, for execution by, or to control the operation of, any suitable data processing apparatus (e.g., a programmable processor, controller, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, subprograms, or portions of code).

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. The processors can be employed by of the components, units or modules of the surgical virtual reality user interface generating system 10 of the present invention. Generally, the processor receives instructions and data from a suitable memory or storage device, such as for example a read-only memory or a random access memory or both. Each of the units of the surgical virtual reality user interface generating system 10 can be structured or include one or more computing devices, and the computing device can include a processor for executing instructions and one or more memory devices for storing instructions and data. Generally, the computing device can also include, or be operatively coupled to receive data from or transfer data to, or both, one or more mass storage devices for storing data, such as for example magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

The system 10 can employ or include any selected type or form of user input device and display unit. The units or components of the system 10 can also communicate as is known over any selected type of network employing one or more computing devices, such as a client device or a server. The network can include any selected type of network such as for example a local area network (LAN), a wide area network (WAN), the Internet, and the like. The system 10 can also communicate over various other forms of communication known in the arm for communicating between disparate parts of a system including SPI, USART, UART, USB, I2C and asynchronous methods, and the like.

Figure 14:
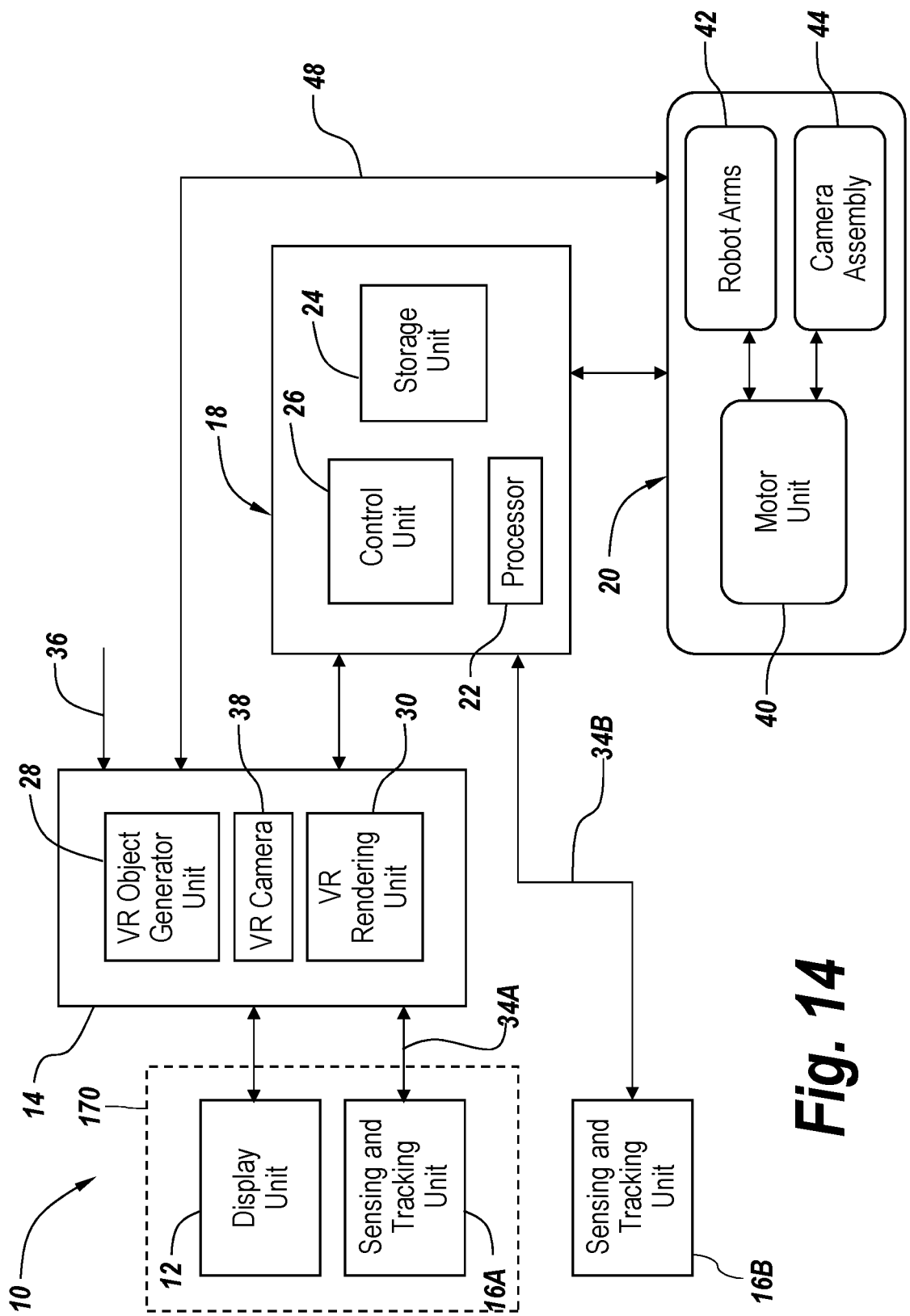
FIG. 14 is a schematic block diagram description of another embodiment of the surgical virtual reality user interface generating system according to the teachings of the present invention.

FIG. 14 shows another embodiment of the surgical virtual reality user interface generating system 10 of the present invention. Like reference numerals denote like parts throughout the various views. In the current embodiment, the system 10 employs a head mounted display 170 that can include the display unit 12 as well as the first of a pair of sensing and tracking units 16A. The head mounted display 170 thus tracks the movements of the head and eyes of the user, and generates tracking and position data 34A that is conveyed to the VR computing unit 14. The tracking and position data 34A is processed by the VR computing unit 14 and the computing unit 18, and in response the control unit 26 generates control signals for controlling movement of the camera assembly 44 of the surgical robot system 20. The system also employs a second sensing and tracking unit 16B that senses and tracks the position of the arms and hands of the user, as described above. The sensing and tracking unit 16B generates tracking and position data 34B that is conveyed to the computing unit 18 and processed by the computing unit 18. In response, the control unit 26 generates control signals for controlling movement of the robot arms 42.

Figure 15:
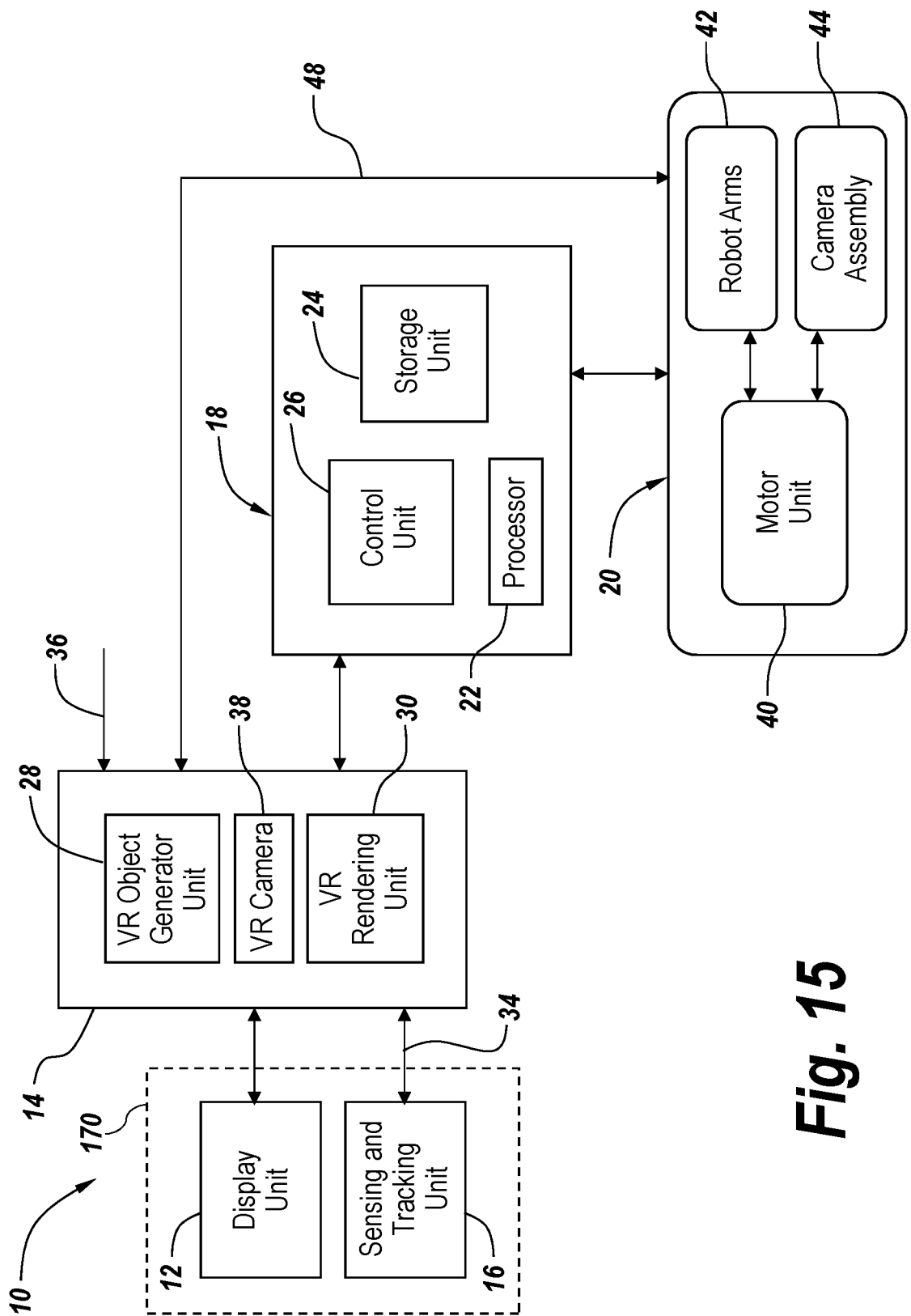
FIG. 15 is a schematic block diagram description of yet another embodiment of the surgical virtual reality user interface generating system according to the teachings of the present invention.

FIG. 15 shows yet another embodiment of the surgical virtual reality user interface generating system of the present invention. Like reference numerals denote like parts throughout the various views. In the current embodiment, the sensing and tracking unit 16 and the display unit 12 form part of a head mounted display 170. The head mounted display 170 thus tracks the movements of the head and eyes of the user, and generates tracking and position data 34A that is conveyed to the VR computing unit 14, which in turn relays the tracking and position data 34 to the computing unit 18 for further processing. In response, the control unit 26 generates control signals for controlling the surgical robot unit 20.

It is contemplated that systems, devices, methods, and processes of the disclosure invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present disclosure that consist essentially of, or consist of, the recited components, and that there are processes and methods according to the present disclosure that consist essentially of, or consist of, the recited processing steps.

It should be understood that the order of steps or order for performing certain action is immaterial so long as the disclosure remains operable. Moreover, two or more steps or actions may be conducted simultaneously. The mention herein of any publication, for example, in the Background section, is not an admission that the publication serves as prior art with respect to any of the claims presented herein. The Background section is presented for purposes of clarity and is not meant as a description of prior art with respect to any claim.

It is to be understood that the disclosed subject matter is not limited in its application to the details of construction and to the arrangements of the components set forth above or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter.

We claim:

1. A surgical virtual reality user interface generating system, comprising
   a sensor and tracking unit for sensing and tracking a position of a portion of a user in space and for generating at least position data based on movement of the user;
   a computing unit for receiving the position data, the computing unit having:
      a processor for processing the position data, and
      a control unit for generating control signals in response to the processed position data;
   a surgical robot system coupled to the computing unit for receiving the control signals and having a camera assembly having a pair of axially spaced apart cameras for generating image data;
   a virtual reality computing unit for generating a virtual reality world, the virtual reality computing unit including:
      a virtual reality rendering unit for receiving at least the image data from the camera assembly and generating an output rendering signal for rendering the image data for display, and
      a virtual reality object generating unit for:
         generating one or more virtual reality informational objects;
         generating a docking station in the virtual reality world, the docking station configured to include a plurality of slots, each of which is configured to house at least one of the one or more virtual reality informational objects; and
         emplacing at least one of the one or more virtual reality informational objects in the docking station or removing at least one of the one or more virtual reality informational objects from the docking station; and
   a display unit for displaying the virtual reality world including the docking station, the one or more virtual reality informational objects, and the image data from the output rendering signal to the user.

2. The system of claim 1, wherein the surgical robot system further comprises:
   one or more robotic arms; and
   a motor unit coupled to the camera assembly and to the one or more robotic arms for selectively moving the camera assembly and the one or more robotic arms in response to the control signals.

3. The system of claim 1, wherein the sensor and tracking unit comprises a hand controller or a head mounted display.

4. The system of claim 3, wherein the hand controller comprises an elongated main body having a movable lever switch coupled thereto.

5. The system of claim 4, wherein the movable lever switch is rotatable about the main body, and wherein the main body has:
   a channel formed therein and the movable lever switch is rotatably mounted in the channel; and
   a finger loop attached thereto.

6. The system of claim 5, further comprising:
   a rest nub formed on the main body; and
   a plurality of actuatable buttons formed on the main body, wherein the plurality of actuatable buttons comprises:
      first and second elbow buttons for allowing, when actuated, the user to manipulate an elbow joint region of one or more robotic arms of the surgical robot system,
      an actuatable rest button for allowing the user, upon actuation, to decouple movement of the one or more robotic arms relative to movement of an arm of the user, and
      a lock button that allows the user to lock the movable lever switch relative to the main body.

7. The system of claim 1, wherein the surgical robot system generates camera data indicative of the position and orientation of the cameras of the camera assembly, and wherein the image rendering unit renders the image data with the camera data.

8. The system of claim 7, wherein the display unit generates display data indicative of the position and orientation of a head of the user, and wherein the VR rendering unit renders the image data with the display data.

9. The system of claim 1, wherein the virtual reality object generating unit is configured to receive informational data from a data source and then implant the informational data in the one or more virtual reality informational objects.

10. The system of claim 9, wherein the informational data comprises data from the surgical robot system.

11. The system of claim 10, wherein the informational data further comprises data from one or more external data sources, and wherein the informational data from the external data sources can comprise one of video data from an external camera or informational data from one or more external medical devices.

12. The system of claim 9, wherein each virtual reality informational object of the one or more virtual reality informational objects is configured to be displayed in the virtual reality world in a free mode where the informational object is disposed at a selected fixed location, a docking mode where the virtual reality informational object is disposed in the docking station, or an attached mode where the virtual reality informational object is disposed so as to follow the user in the virtual reality world.

13. The system of claim 12, wherein when a virtual reality informational object is removed from a slot of the docking station by the user, the virtual reality informational object is automatically switched to the free mode.

14. The system of claim 1, wherein the virtual reality object generating unit generates an object list having a list of the one or more virtual reality informational objects, wherein each of the one or more virtual reality informational objects in the object list includes a title of the virtual reality informational object.

15. The system of claim 1, wherein each virtual reality informational object of the one or more virtual reality informational objects includes a title bar and a content region for displaying data, wherein the title bar includes a title of the virtual reality informational object and a plurality of action buttons.

16. The system of claim 15, wherein the plurality of action buttons comprises two or more of an auto visibility button which allow the user to determine if the virtual reality informational object is visible or not in the virtual world, an object mode button that allows the user to switch object modes, a docking station button that allows the user to move the virtual reality informational object into the docking station, and a close button that hides the virtual reality informational object.

17. The system of claim 1, wherein the virtual reality computing unit further comprises a photosphere generation unit for generating a photosphere from the image data.

18. The system of claim 17, wherein the control unit is configured to generate an autoscan signal that is received by the camera assembly, and the camera assembly in response operates in an autoscan mode where the cameras in the camera assembly autonomously rotate through an entire range of motion to capture the image data.

19. The system of claim 1, wherein the virtual reality computing unit further comprises a scene graph generating unit for generating a scene graph, wherein the scene graph includes a plurality of nodes arranged in a tree graph structure.

20. A method of generating one or more informational objects, comprising:
sensing and tracking at least a position of a portion of a user in space and for generating position data based on movement of the user;
providing a computing unit for receiving and processing the position data and generating control signals in response to the processed position data;
providing a surgical robot system for receiving the control signals and having a camera assembly having a pair of axially spaced apart cameras for generating image data
generating a virtual reality world with a virtual reality computing unit, where the virtual reality computing unit includes:
a virtual reality rendering unit for receiving at least the image data from the camera assembly and generating an output rendering signal for rendering the image data for display, and
a virtual reality object generating unit for:
generating one or more virtual reality informational objects;
generating a docking station in the virtual reality world, the docking station configured to include a plurality of slots, each of which is configured to house at least one of the one or more virtual reality informational objects; and
emplacing at least one of the one or more virtual reality informational objects in the docking station or removing at least one of the one or more virtual reality informational objects from the docking station; and
displaying the virtual reality world including the docking station, the one or more virtual reality informational objects, and the image data from the output rendering signal to the user.

21. The method of claim 20, wherein the surgical robot system further comprises:
one or more robotic arms; and
a motor unit coupled to the camera assembly and to the one or more robotic arms for selectively moving the camera assembly and the one or more robotic arms in response to the control signals.

22. The method of claim 20, wherein the sensor and tracking unit comprises a hand controller or a head mounted display.

23. The method of claim 22, wherein the hand controller comprises an elongated main body having a movable lever switch coupled thereto, and wherein the movable lever switch is rotatable about the main body, and wherein the main body has a channel formed therein and the lever switch is rotatably mounted in the channel.

24. The method of claim 23, further comprising providing a plurality of actuatable buttons formed on the main body, and wherein the plurality of actuatable buttons comprises:
first and second elbow buttons for allowing when actuated the user to manipulate an elbow joint region of one or more robotic arms of the surgical robot system;
an actuatable rest button for allowing the user, upon actuation, to decouple movement of the one or more robotic arms relative to movement of an arm of the user; and
a lock button that allows the user to lock the movable lever switch relative to the main body.

25. The method of claim 20, wherein the virtual reality object generating unit is configured to receive informational data from a data source and then implant the informational data in the one or more virtual reality informational objects.

26. The method of claim 25, wherein the informational data comprises data from the surgical robot system.

27. The method of claim 26, wherein the informational data further comprises data from one or more external data sources, and wherein the informational data from the one or more external data sources comprises one of video data from an external camera or informational data from one or more external medical devices.

28. The method of claim 25, wherein each virtual reality informational object of the one or more virtual reality informational objects is configured to be displayed in the virtual reality world in a free mode where the virtual reality informational object is disposed at a selected fixed location, a docking mode where the virtual reality informational object is disposed in the docking station, or an attached mode where the virtual reality informational object is disposed so as to follow the user in the virtual reality world.

29. The method of claim 28, wherein when a virtual reality informational object is removed from a slot of the docking station by the user, the virtual reality informational object is automatically switched to the free mode.

30. The method of claim 20, comprises generating, by the virtual reality object generating unit, an object list having a list of the one or more virtual reality informational objects, wherein each of the one or more virtual reality informational objects in the object list includes a title of the virtual reality informational object.

31. The method of claim 20, wherein each virtual reality informational object of the one or more virtual reality informational objects includes a title bar and a content region for displaying data, wherein the title bar includes a title of the virtual reality informational object and a plurality of action buttons.

32. The method of claim 31, wherein the plurality of action buttons comprises two or more of an auto visibility button which allow the user to determine if the virtual reality informational object is visible or not in the virtual world, an object mode button that allows the user to switch object modes, a docking station button that allows the user to move the virtual reality informational object into the docking station, and a close button that hides the virtual reality informational object.

33. The method of claim 20, wherein the virtual reality computing unit comprises a photosphere generation unit for generating a photosphere from the image data.

34. The method of claim 33, comprises:
  generating, by the control unit, an autoscan signal that is received by the camera assembly; and
  operating the camera assembly, in response, in an autoscan mode where the cameras in the camera assembly autonomously rotate through an entire range of motion to capture the image data.

* * * * *